(12) United States Patent
Santos et al.

(10) Patent No.: US 10,730,901 B2
(45) Date of Patent: Aug. 4, 2020

(54) SPINOSYN FORMULATIONS FOR TREATMENT OF DEMODEX-INDUCED OCULAR AND FACIAL CONDITIONS

(71) Applicant: APERTA BIOSCIENCES, LLC, Saint Louis, MO (US)

(72) Inventors: Carlos Santos, Austin, TX (US); Iuan-Bor Chen, Bowmanville (CA); Josue Moran, Austin, TX (US)

(73) Assignee: APERTA BIOSCIENCES, LLC, Saint Louis, MO (US)

( * ) Notice: Subject to any disclaimer, the term of this patent is extended or adjusted under 35 U.S.C. 154(b) by 0 days.

(21) Appl. No.: 16/523,984

(22) Filed: Jul. 26, 2019

(65) Prior Publication Data
US 2020/0031859 A1  Jan. 30, 2020

Related U.S. Application Data

(60) Provisional application No. 62/711,309, filed on Jul. 27, 2018.

(51) Int. Cl.
| | |
|---|---|
| C07H 17/08 | (2006.01) |
| A61K 9/00 | (2006.01) |
| A61K 9/107 | (2006.01) |
| A61K 47/10 | (2017.01) |
| A61K 47/44 | (2017.01) |
| A61K 47/14 | (2017.01) |
| A61K 47/32 | (2006.01) |
| A61K 8/37 | (2006.01) |
| A61K 8/368 | (2006.01) |
| A61K 8/92 | (2006.01) |
| A61K 8/81 | (2006.01) |
| A61K 8/34 | (2006.01) |
| A61K 47/12 | (2006.01) |
| A61K 45/06 | (2006.01) |

(52) U.S. Cl.
CPC .......... *C07H 17/08* (2013.01); *A61K 8/342* (2013.01); *A61K 8/368* (2013.01); *A61K 8/37* (2013.01); *A61K 8/8176* (2013.01); *A61K 8/92* (2013.01); *A61K 9/0014* (2013.01); *A61K 9/107* (2013.01); *A61K 47/10* (2013.01); *A61K 47/12* (2013.01); *A61K 47/14* (2013.01); *A61K 47/32* (2013.01); *A61K 47/44* (2013.01); *A61K 45/06* (2013.01)

(58) Field of Classification Search
None
See application file for complete search history.

(56) References Cited

U.S. PATENT DOCUMENTS

| | | |
|---|---|---|
| 2,348,930 A | 5/1944 | Schepmoes |
| 3,934,023 A | 1/1976 | Okuno et al. |
| 4,113,968 A | 9/1978 | Mori et al. |
| 5,202,242 A | 4/1993 | Mynderse et al. |
| 5,362,634 A | 11/1994 | Boeck et al. |
| 5,496,931 A | 3/1996 | Boeck et al. |
| 5,571,901 A | 11/1996 | Boeck et al. |
| 5,591,606 A | 1/1997 | Turner et al. |
| 5,631,155 A | 5/1997 | Turner et al. |
| 5,670,364 A | 9/1997 | Mynderse et al. |
| 5,670,486 A | 9/1997 | Mynderse et al. |
| 5,767,253 A | 6/1998 | Turner et al. |
| 5,840,861 A | 11/1998 | Mynderse et al. |
| 7,709,447 B2 | 5/2010 | Hacket et al. |
| 8,128,968 B2 | 3/2012 | Gao et al. |
| 8,536,142 B2 | 9/2013 | Hacket et al. |
| 8,546,357 B2 | 10/2013 | Akama et al. |
| 8,697,661 B2 | 4/2014 | Kritikou |
| 9,000,026 B2 | 4/2015 | Liu et al. |
| 9,788,994 B2 | 10/2017 | Nichamin |
| 9,895,388 B1 | 2/2018 | Mettert et al. |
| 2002/0064513 A1 | 5/2002 | Maitra et al. |
| 2008/0275107 A1* | 11/2008 | Spring ............... A01N 25/04 514/450 |
| 2009/0093421 A1 | 4/2009 | Kaoukhov et al. |
| 2010/0075956 A1 | 3/2010 | Critcher et al. |
| 2010/0093652 A1 | 4/2010 | Spring et al. |
| 2012/0195961 A1 | 8/2012 | Kritikou et al. |
| 2016/0184340 A1 | 6/2016 | Kritikou |
| 2016/0361297 A1 | 12/2016 | Soll et al. |
| 2019/0183862 A1 | 6/2019 | Azamian et al. |

FOREIGN PATENT DOCUMENTS

| | | |
|---|---|---|
| CN | 101137369 | 3/2008 |
| CN | 101801387 | 8/2010 |
| CN | 102844047 | 12/2012 |
| CN | 103478145 | 1/2014 |

(Continued)

OTHER PUBLICATIONS

International Search Report and Written Opinion for PCT/US2019/043809, dated Oct. 18, 2019.
Akçinar U.G. et al. "*Demodex* spp. Infestation Associated with Treatment-Resistant Chalazia and Folliculitis" *Turkiye Parazito Derg*, 2016, pp. 208-210, vol. 40 (English Abstract).
How to Prescribe Avenova®, [online, webpage, retrieved Aug. 2, 2019] from: http://avenova.com/physician/, pp. 1-3.
Chalazion: Causes, Risk Factors, and Symptoms, [online, webpage, retrieved Aug. 2, 2019] from: www.healthline.com/health/chalazion, pp. 1-15.
Damian, D, et al. "*Demodex* infestation in a child with leukaemia: treatment with ivermectin and permethrin" *Int J Dermatol.*, 2003, pp. 724-726, vol. 42.
Elston, D.M. "*Demodex* mites: Facts and controversies" *Clin Dermatol*, 2010, pp. 502-504, vol. 28, No. 5.

(Continued)

*Primary Examiner* — Robert S Cabral
(74) *Attorney, Agent, or Firm* — Saliwanchik, LLoyd & Eisenschenk

(57) ABSTRACT

The present invention concerns materials and methods for treating an ocular *Demodex* mite infestation of an eye of a human or animal subject, or for treating a condition of the eye or skin associated with ocular *Demodex* mite infestation, the method comprising topically administering a composition comprising one or more spinosyn compounds to the ocular surface (conjunctiva and/or cornea) or other anatomical structure of the eye, or to an area adjacent the eye.

20 Claims, 1 Drawing Sheet

(56) References Cited

FOREIGN PATENT DOCUMENTS

| CN | 104619352 | 5/2015 |
|---|---|---|
| WO | WO 1993/009126 | 5/1993 |
| WO | WO 1994/020518 | 9/1994 |
| WO | WO 2007/054822 | 5/2007 |
| WO | WO 2013/090891 | 6/2013 |
| WO | WO 2016/070134 | 5/2016 |

OTHER PUBLICATIONS

Gao, Y-Y et al. "In vitro and in vivo killing of ocular *Demodex* by tea tree oil" *Br J Ophthalmol*, 2005, pp. 1468-1473, vol. 89.

Grice, E.A. "The skin microbiome: potential for novel diagnostic and therapeutic approaches to cutaneous disease" *Semin Cutan Med Surg.*, 2014, pp. 98-103, vol. 33, No. 2.

Hasegawa, T. "A case report of the management of demodicosis in the golden hamster" *J Vet Med Sci*, 1995, pp. 337-338, vol. 57, No. 2.

Hu, L. et al., "Molecular identification of four phenotypes of human *Demodex* in China," *Exp Parisitol*, 2014, pp. 38-42, vol. 142.

Jimenez-Acosta, F. et al. "*Demodex* mites contain immunoreactive lipase" *Arch Dermato*, 1989, pp. 1436-1437, vol. 125, No. 10, Abstract.

Kasetsuwan, N. et al. "Prevalence of ocular demodicosis among patients at Tertiary Care Center, Bangkok, Thailand" *Int J Ophthalmol*, 2017, pp. 122-127, vol. 10, No. 1.

Kirst, H.A. etal. "A83543A-D, Unique Fermentation-Derived Tetracyclic Macrolides" *Tetrahedron Letters*, 1991, pp. 4839-4842, vol. 32, No. 37.

Kirst, H.A. "The spinosyn family of insecticides: realizing the potential of natural products research" *The Journal of Antibiotics*, 2010, pp. 101-111, vol. 63.

Lacey, N. et al. "Under the lash: *Demodex* mites in human diseases" *Biochem (Lond).*, 2009, pp. 2-6, vol. 31, No. 4.

Legocki, J et al. "Contemporary trends in development of active substances possessing the pesticidal properties: spinosyn insecticides" *Pestycydy/Pesticides*, 2010, pp. 59-71, vol. 1, No. 4.

Li, J. et al. "Correlation between ocular Demodex infestation and serum immunoreactivity to *Bacillus* proteins in patients with facial rosacea" *Ophthalmology*, 2010, pp. 870-877, vol. 117, No. 5.

Liang, L, et al. High Prevalence of *Demodex* Brevis Infestation in Chalazia, *Am J Ophthalmol.*, 2014, pp. 343-347, vol. 157, No. 2.

Litwin, D. et al. "Human Permanent Ectoparasites; Recent Advances on Biology and Clinical Significance of *Demodex* Mites: Narrative Review Article" *Iran J Parasitol*, Jan.-Mar. 2017, pp. 12-21, vol. 12, No. 1.

Liu, J. et al. "Pathogenic role of *Demodex* mites in blepharitis" *Curr Opin Allergy Clin Immunol.*, 2010, pp. 505-510, vol. 10, No. 5.

Nyak, D.M. "Demodectic Rosaceae in a Diabetic Patient" International Journal of Scientific and Research Publications, Feb. 2013, pp. 1-2, vol. 3, No. 2, ISSN 2250-3153.

Randon, M. et al. "In vivo confocal microscopy as a novel and reliable tool for the diagnosis of *Demodex* eyelid infestation" *Br J Ophthalmol*, 2015, pp. 336-341, vol. 99, No. 3.

Rather, P.A. et al. "Human *Demodex* Mite: The Versatile Mite of Dermatological Importance" *Indian J Dermatol*, 2014, pp. 60-66, vol. 59, No. 1.

Salgado, V.L. et al. "Studies on the Mode of Action of Spinosad: The Internal Effective Concentration and the Concentration Dependence of Neural Excitation" *Pesticide Biochemistry and Physiology*, 1998, pp. 103-110, vol. 60.

Schear, M.J. et al. "The Association of *Demodex* with Chalazia: A Histopathologic Study of the Eyelid" *Ophthalmic Plast Reconstr Surg.*, 2016, pp. 275-278, vol. 32, No. 4.

Sparks, T.C. et al. "Natural products as insecticides: the biology, biochemistry and quantitative structure-activity relationships of spinosyns and spinosoids" *Pest Manag Sci*, 2001, pp. 896-905, vol. 57.

Szkaradkiewicz, A. et al. "*Bacillus oleronius* and *Demodex* mite infestation in patients with chronic blepharitis" *Clinical Microbiology and Infection*, 2012, pp. 1020-1025, vol. 18, No. 10.

Tarkowski, W. et al. *Demodex* mites as potential etiological factor in chalazion—a study in Poland, *Acta Parasitol*, 2015, pp. 777-783, ISSN 1230-2821.

Tighe, S et al. "Terpinen-4-ol is the Most Active Ingredient of Tea Tree Oil to Kill *Demodex* Mites," *Trans Vis Sci Tech.*, 2013, pp. 1-8, vol. 2, No. 7, Article 2.

Yam, J.C. et al. "Ocular Demodicidosis as a Risk Factor of Adult Recurrent Chalazion" *Eur J Ophthalmol.*, 2014, Abstract.

Zhao, Y. et al. "Cloning and sequence analysis of chitin synthase gene fragments of *Demodex* mites" *J Zheijang Univ-Sci B*, 2012, pp. 763-768, vol. 13, No. 10.

Zhao, Y. et al. "Discrimination between *Demodex folliculorum* (Acari: Demodicidae) isolates from China and Spain based on mitochondrial cox1 sequences," *J Zheijang Univ-Sci B*, 2013, pp. 829-836, vol. 14, No. 9.

Ziegelmann, B. et al. "Lithium chloride effectively kills the honey bee parasite *Varma destructor* by a systemic mode of action" *Scientific Reports*, 2018, pp. 1-9, No. 8, Article No. 683.

Mathison, B. and Pritt, B. "Laboratory identification of arthropod ectoparasites" *Clin. Microbiol. Rev.*, 2014, 27(1):48-67.

Serious Eye Damage / Eye Irritation, SCHC Hazard Communication Information Sheet, Mar. 2018.

Entrust Naturalyte Insect Control safety data sheet, Dow AgroSciences, Jun. 2016.

Natroba Topical Suspension prescribing information, ParaPRO LLC, Jan. 2011.

\* cited by examiner

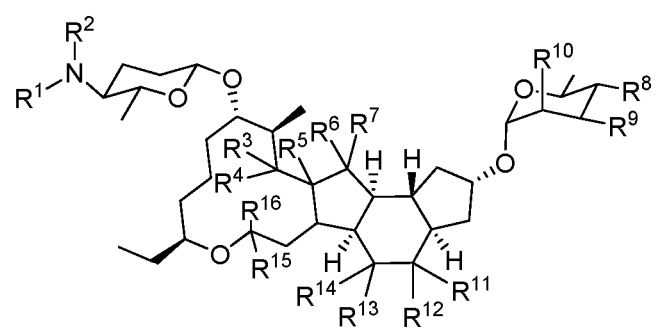

SPINOSYN FORMULATIONS FOR TREATMENT OF DEMODEX-INDUCED OCULAR AND FACIAL CONDITIONS

CROSS-REFERENCE TO RELATED APPLICATION

The present application claims the benefit of U.S. Provisional Application Ser. No. 62/711,309, filed Jul. 27, 2018, which is hereby incorporated by reference herein in its entirety, including any figures, tables, nucleic acid sequences, amino acid sequences, or drawings.

BACKGROUND OF THE INVENTION

*Demodex* is a genus of ecto-parasitic mites within the Arachnida class that live in or near hair follicles of mammals. *Demodex* mites have a commensal relationship with humans, and they asymptomatically parasitize the pilosebaceous follicles of humans. Thus, these mites are part of the normal microbiome in the sebaceous areas of the skin in humans (Grice E A et al., "The skin microbiome: potential for novel diagnostic and therapeutic approaches to cutaneous disease," *Semin Cutan Med Surg.,* 2014, 33(2):98-103). In healthy skin, the density of the mites is normally low, and this low density does not cause skin diseases. When the density of these mites increases, they induce facial skin conditions. Patients with an ocular *Demodex* infestation often complain of itching, burning, redness, crusting at the base of the lashes, blurry vision and dry eye.

Among the over 100 species of *Demodex* mites that have been identified, *Demodex folliculorum* and *Demodex brevis* are the two main species commonly found on humans (Lacey N et al., "Under the lash: *Demodex* mites in human diseases," *Biochem* (Lond)., 2009 Aug. 1, 31(4):2-6). Most individuals become colonized during childhood and numbers proliferate in and around the pilosebaceous units at the age of puberty as levels of secreted sebum increase, and increasing in prevalence with age (Elston D M, "*Demodex* mites: facts and controversies", *Clin Dermatol,* 2010, 28(5): 502-504). This may be due to lipases produced by *Demodex*, allowing the mite to utilize sebum as a food source (Jimenez-Acosta F et al., "*Demodex* mites contain immunoreactive lipase", *Arch Dermatol,* 1989, 125(10):1436-1437). Other nutritional sources include cellular debris and bacteria that reside in and around the pilosebaceous unit.

*D. folliculorum* has a comparatively long body and proliferates at the base of the lashes (cylindrical dandruff), causing anterior blepharitis. Specifically, *D. folliculorum* consume epithelial cells at the hair follicle causing lash distention, hypoplasia, and reactive hyperkeratinization, which is commonly observed as trichiasis and madarosis. *D. brevis* is shorter in size and burrows into the sebaceous and meibomian glands, causing posterior blepharitis. *D. brevis* obstructs meibomian gland openings, leading to insufficient tear lipid secretion, which can be an inflammatory trigger for dry eye.

*Demodex* mites also carry their own bacterial reservoirs that can contribute to ocular surface inflammation. The bacteria on the surface of the mite has been shown to compete with known staphylococcal species, producing a human host immune response leading to an inflammatory eyelid and periorbital epidermal to subepidermal reaction. If the disease is in a chronic and progressive phase, the inflammation may spread to the conjunctiva and cornea, potentially leading to infiltrative keratoconjunctivitis, nodular scar deposition and corneal neovascularization.

BRIEF SUMMARY OF THE INVENTION

The present invention concerns materials and methods for treating an ocular *Demodex* mite infestation of an eye of a human or animal subject, or for treating a condition of the eye or skin associated with ocular *Demodex* mite infestation, such as *Demodex folliculorum, Demodex brevis*, or both.

One aspect of the invention concerns a method for treating an ocular *Demodex* mite infestation of an eye of a human or animal subject, or for treating a condition of the eye or skin associated with ocular *Demodex* mite infestation, comprising topically administering a composition comprising one or more spinosyn compounds to the ocular surface (conjunctiva and/or cornea) or other anatomical structure of the eye, or to an area adjacent the eye. In some embodiments, the condition is one or more from among *Demodex*-induced blepharitis (also called *Demodex* blepharitis), *Demodex*-induced ocular rosacea, *Demodex*-induced facial rosacea, dry eye, meibomian gland dysfunction, chalazion, hordeolum, follicular inflammation, non-specific facial dermatitis, infiltrative keratoconjunctivitis, nodular scar deposition, or corneal neovascularization. The treatment can alleviate one or more signs or symptoms in the subject selected from among: itching, burning, foreign body sensation, crusting and redness of the lid margin, blurry vision, cylindrical dandruff, eyelash misalignment, eyelash trichiasis, eyelash madarosis, lid margin inflammation, meibomian gland dysfunction, blepharoconjunctivitis, and blepharokeratitis in the subject.

In some embodiments, the composition is topically administered to an area adjacent to the eye, wherein the area comprises one or more of an eyelid, eyelid margin, eyelashes, eyelash follicles, eyebrow, or eyebrow follicles. In some embodiments, the composition is topically administered to an area adjacent to the eye, wherein the area comprises a sebaceous gland opening of the eyelid (e.g., one or more of gland of Zeis, gland of Moll, or Meibomian gland).

Another aspect of the invention concerns a topical composition comprising 0.1% to 10% (w/v) of the one or more spinosyn compounds (also referred to herein as the "topical composition" or "spinosyn composition", or "topical spinosyn composition" of the invention), and methods for making the topical composition. In some embodiments, the composition is a solution, suspension, salve, spray, lotion, gel, paste, balm, foam, mousse, scrub or cleanser (e.g., shampoo or soap), cream, or ointment. Soaps may be solid, such as a bar, liquid, or semi-solid.

Another aspect of the invention concerns an article of manufacture comprising the topical composition; and a container with the topical composition contained therein. In some embodiments, the container is a collapsible or non-collapsible tube, bag, packet, blister, strip, ampoule, viral, bottle, can, or jar.

Another aspect of the invention concerns an ocular or facial applicator pre-treated with, or containing, the topical composition. In some embodiments, the applicator is a swab, cosmetic pad, wipe, wipe stick, towelette, sponge, gauze, puff, wand, brush, or comb.

Another aspect of the invention concerns a kit useful for treating an ocular *Demodex* mite infestation of an eye of a human or animal subject, or for treating a condition of the eye or skin associated with ocular *Demodex* mite infestation, such as *Demodex folliculorum, Demodex brevis*, or both.

The kit comprises the topical composition; and an ocular or facial applicator. Optionally, the applicator may be pre-treated with, or contain the topical composition. The kit may further include a container containing the composition. The kit may further include instructions (e.g., printed or digital instructions) for treating an ocular *Demodex* mite infestation of an eye of a human or animal subject, or for treating a condition of the eye or skin associated with ocular *Demodex* mite infestation, by topically administering the composition to the ocular surface (conjunctiva and/or cornea) or other anatomical structure of the eye, or to an area adjacent the eye.

BRIEF DESCRIPTION OF THE DRAWINGS

FIG. 1 shows the chemical structure (Formula (I)) of some embodiments of spinosyn compounds that may be used in the compositions and methods of the inventions.

DETAILED DESCRIPTION OF THE INVENTION

The present invention concerns materials and methods for treating an ocular *Demodex* mite infestation of an eye of a human or animal subject, or for treating a condition of the eye or skin associated with ocular *Demodex* mite infestation, such as *Demodex folliculorum, Demodex brevis*, or both. One aspect of the invention concerns a topical composition useful for treating an ocular *Demodex* mite infestation of an eye of a human or animal subject, or for treating a condition of the eye or skin associated with ocular *Demodex* mite infestation, the composition comprising 0.1% to 10% (w/v) of the one or more spinosyn compounds.

The fermentation product identified in U.S. Pat. No. 5,362,634 as A83543 is a family of related compounds produced by *Saccharopolyspora spinosa*. These compounds have been referred to as factors or components A, B, C, D, E, F, G, H, J, K, L, M, N, O, P, Q, R, S, T, U, V, W, Y, and the like (also see published international patent application WO 93/09126 and WO 94/20518) and are referred to as spinosyn A, B, C, and so on. Spinosyns are a family of macrocyclic lactones having pesticidal activity on a variety of pests. The early identified spinosyns were found to have a 5,6,5-tricylic ring system, fused to a 12-membered macrocyclic lactone, a neutral sugar (rhamnose), and an amino sugar (forosamine) (see Kirst, H. A. et al. (1991) "A83543A-D, Unique Fermentation-Derived Tetracyclic Macrolides" Tetrahedron Letters 32(37):4839-4842). Natural spinosyns may be produced via fermentation from cultures deposited as NRRL 18719, 18537, 18538, 18539, 18743, 18395, and 18823 of the stock culture collection of the Midwest Area Northern Regional Research Center, Agricultural Research Service, United States Department of Agriculture, 1815 North University Street, Peoria, Ill. 61604. Spinosyns are also disclosed in U.S. Pat. Nos. 5,496,931, 5,670,364, 5,591, 606, 5,571,901, 5,202,242, 5,767,253, 5,840,861, 5,670,486 and 5,631,155. Spinosyns have been found useful for the control of arachnids, nematodes, and insects.

Examples of spinosyns and spinosoids (semi-synthetic analogs) are disclosed in Kirst H A, "The spinosyn family of insecticides: realizing the potential of natural products research," *The Journal of Antibiotics*, 2010, 63:101-111; Legocki J et al., "Contemporary trends in development of active substances possessing the pesticidal properties: spinosyn insecticides," *Pestcydy/Pesticides*, 2010, 1-4:59-71; Sparks T C et al., "Natural products as insecticides: the biology, biochemistry and quantitative structure-activity relationships of spinosyns and spinosoids", *Pest Manag Sci*, 2001, 57:896-905; and Salgado V L et al., "Studies on the Mode of Action of Spinosad: The Internal Effective Concentration and the Concentration Dependence of Neural Excitation," *Pesticide Biochemistry and Physiology,"* 1998, 60:103-110, which are each incorporated herein by reference in their entirety).

Spinosyn compounds useful in the various aspects and embodiments of the invention refer to spinosyns and spinosoids having miticidal activity against members of the *Demodex* genus. The terms "acaricidal" and "miticidal" are used herein interchangeably to refer to the ability to kill mites of the *Demodex* genus in any life stage, or the ability to interfere with a *Demodex* mite's growth or life cycle in any way that results in an overall reduction in *Demodex* mite population. In some embodiments, the *Demodex* species is *D. folliculorum, D. brevis*, or both. For example, the term "miticidal" includes inhibition or elimination of reproductive ability of a pest, as well as inhibition of a pest from progressing from one form to a more mature form, e.g., transition between various larval forms or transition from larvae to proto-nymph or from proto-nymph to nymph, or from nymph to adult. Further, the term miticidal is intended to include all phases of a mite life cycle; thus, for example, the term includes larvicidal, ovicidal, and adulticidal action (see, for example, Rather P. A. et al., Human *Demodex* Mite: The Versatile Mite of Dermatological Importance", *Indian J Dermatol*, 2014, January-February, 59(1):60-66). Techniques for assessing in vitro and in vivo *Demodex* killing activity are known in the art and may be utilized (see, for example, U.S. Pat. No. 8,128,968 (Gao et al.); Gao Y-Y et al., "In vitro and in vivo killing of ocular *Demodex* by tea tree oil," *Br J Ophthalmol*, 2005, 89:1468-1473; and Tighe S et al., "Terpinen-4-ol is the most active ingredient of tea tree oil to kill *Demodex* mites," *Trans Vis Sci Tech.*, 2013, 2(7):2).

In some embodiments, the one or more spinosyn compounds have the chemical structure of Formula (I), shown in FIG. 1, or a pharmaceutically acceptable salt thereof, where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, can be independently selected from the group consisting of: null; H; F; Cl; Br; I; OH; CN; $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid (—$SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (=O); ether (—$OR^{17}$); and ester (—$COOR^{18}$ and —$OC(=O)R^{18}$);

where $R^5$ and $R^7$ can be a double bond within the cyclopentane ring;

where $R^{11}$ and $R^{13}$ can be a double bond within the cyclohexane ring;

where $R^{17}$ can be independently selected from the group consisting of: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl;

where $R^{18}$ can be independently selected from the group consisting of: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl.

In some embodiments, the composition comprises spinosyn A, spinosyn D, or a combination thereof. The chemical structures of these and many other spinosyn compounds have been known for some time. Spinosyn A has the following substituent atoms or groups in the structure of Formula (I): $R^1$, $R^2=(C_{1-4})$alkyl, namely methyl; $R^3$=ketone (=O); $R^4$=null; $R^5$ and $R^7$ are a double bond within the cyclopentane ring; $R^8$, $R^9$, $R^{10}$=—$OR^{17}$, namely —$OCH_3$; $R^{11}$ and $R^{13}$ are a double bond within the cyclohexane ring; $R^{12}$ and $R^{14}$ are H; $R^{15}$=null; and $R^{16}$=ketone (=O). Spinosyn D has the following substituent atoms or groups in the structure of Formula (I): $R^1$, $R^2=(C_{1-4})$alkyl, namely methyl; $R^3$=ketone (=O); $R^4$=null; $R^5$ and $R^7$ are a double bond within the cyclopentane ring; $R^8$, $R^9$, $R^{10}$=—$OR^{17}$, namely —$OCH_3$; $R^{11}$ and $R^{13}$ are a double bond within the cyclohexane ring; $R^{12}$ is $(C_{1-4})$alkyl, namely methyl; $R^{14}$ is H; $R^{15}$=null; and $R^{16}$=ketone (=O).

In some embodiments, the spinosyn A and spinosyn D are present in the composition in a ratio of about 18:2 to about 16:4 spinosyn A to spinosyn D. In some embodiments, the spinosyn A and spinosyn D are present in the composition in a ratio of about 17:3 spinosyn A to spinosyn D (spinosad).

The composition may be formulated in any dosage form that is useful for topical administration to the ocular surface (conjunctiva and/or cornea), other anatomical structure of the eye, and/or to an area adjacent the eye, such as an eyelid, eyelid margin, eyelashes, eyelash follicles, eyebrow, or eyebrow follicles, or an area encompassing a sebaceous gland opening of the eyelid (e.g., one or more of gland of Zeis, gland of Moll, or Meibomian gland). In some embodiments, the composition is a solution, suspension, salve, spray, lotion, gel, paste, balm, foam, mousse, scrub or cleanser (e.g., shampoo or soap), cream, or ointment. A soap may be solid, such as a bar, liquid, or semi-solid.

Methods for making dermatologically acceptable and/or ophthalmically acceptable compositions may be employed to mix the one or more spinosyn compounds with one or more additional components of the composition. The components of the composition may be pre-sterilized, or the composition may be sterilized during or at the end of production.

In some embodiments, the composition may be formed as a cosmetic product (e.g., make-up), such as foundation, mascara, eye shadow, or eye liner. The composition may also be in the form of a mask or make-up remover.

In various embodiments, the compositions encompassed herein comprise pharmaceutically acceptable excipients such as those listed in Remington: the Science and Practice of Pharmacy 866-885 (Alfonso R. Gennaro ed. 19th ed. 1995; Ghosh, T. K.; et al. Transdermal And Topical Drug Delivery Systems, which is hereby incorporated by reference herein in its entirety), including, but not limited to, protectives, adsorbents, demulcents, emollients, preservatives, antioxidants, moisturizers, buffering agents, solubilizing agents, skin-penetration agents, and surfactants.

Preferably, the spinosyn composition includes a dermatologically acceptable and/or ophthalmically acceptable base. As used herein, a "dermatologically acceptable base" refers to one or more non-detergent excipients that do not cause irritation, inflammation, pain, or other harm to the skin when applied to the skin adjacent the eye at effective concentrations. As used herein, an "ophthalmically acceptable base" refers to one or more non-detergent excipients that do not irritate or otherwise harm the surface of the eye when topically administered to ocular surface at effective concentrations.

Protectives and adsorbents include, but are not limited to, dusting powders, zinc sterate, collodion, dimethicone, silicones, zinc carbonate, aloe vera gel and other aloe products, vitamin E oil, allantoin, glycerin, petrolatum, and zinc oxide. Demulcents include, but are not limited to, benzoin, hydroxypropyl cellulose, hydroxypropyl methylcellulose, and polyvinyl alcohol. Emollients include, but are not limited to, animal and vegetable fats and oils, myristyl alcohol, alum, and aluminum acetate. Preservatives include, but are not limited to, chlorine dioxide, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other antimicrobial agents such as chlorhexidine, chlorocresol, benzoic acid and polymyxin. Suitable antioxidants include, but are not limited to, ascorbic acid and its esters, sodium bisulfate, butylated hydroxytoluene, butylated hydroxyanisole, tocopherols, and chelating agents like EDTA and citric acid. Suitable moisturizers include, but are not limited to, glycerin, sorbitol, polyethylene glycols, urea, and propylene glycol. Suitable solubilizing agents include, but are not limited to, quaternary ammonium chlorides, cyclodextrins, benzyl benzoate, lecithin, and polysorbates. Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methylpyrrolidone.

The composition may include one or more excipients. In some embodiments, the composition includes one or more excipients selected from among petrolatum, mineral oil, propylparaben, methylparaben, lanolin, chlorobutanol, water, lanolin alcohol, sodium thiosulfate, sodium phosphate monobasic, phenylmercuric acetate, mannitol, zinc chloride, sodium phosphate, potassium acetate, hypromelloses, gentamcicin sulfate, boric acid, sodium hydroxide, lanolin oil, carbomer homopolymer type b (allyl pentaerythritol crosslinked), or benzalkonium chloride. In some embodiments, the composition includes no parabens.

The composition may include a gelling agent. Examples of gelling agents include gum, agar, carrageenan, petrolatum, or a cellulosic polymer (e.g., hydroxyethyl cellulose or hydroxymethyl cellulose).

The composition may further include one or more of a solvent, co-solvent, demulcent, emollient, preservative, antimicrobial agent, antioxidant, moisturizer, stabilizing agent, or solubilizing agent.

In some embodiments, the composition includes one or more excipients selected from among water, sodium hydroxide, polysorbate 80, glycerine, castor oil, sodium acetate, boric acid, sorbic acid, edetate disodium, carbomer copolymer type A or B (allyl pentaerythritol crosslinked), or silicone oil or silicone polymer gel (e.g., dimethicone or cyclomethicone).

Mucoadhesive polymers that provide localized delivery of the active ingredient to the anatomical target site may be included, and are especially useful in gels. Such polymers have a property known as bioadhesion, which refers to the capacity for a drug carrier to a specific biological tissue, such as a mucous membrane. These polymers can extend the contact time of the active agent with the biological tissue and thereby improve bioavailability. Examples of bioadhesive polymers having various mucoadhesive performance qualities include carboxymethylcellulose, carbopol, polycarbophil, and sodium alginate.

The pH of the spinosyn composition should be in a dermatologically and/or ophthalmically acceptable range. Normal tears have a pH of about 7.4 and possess some buffer capacity. The administration of a composition to the eye stimulates the flow of tears and the rapid neutralization of any excess hydrogen or hydroxyl ions within the buffer capacity of the tears. Where only 1 or 2 drops of a liquid composition containing an active agent are added to the eye, the buffering action of the tears is usually adequate to raise the pH and prevent marked discomfort.

While it is desirable for an ophthalmic composition to have the same pH and isotonic value as lacrimal fluid, this is not usually possible. The buffer system should be selected that is nearest to the physiological pH of 7.4 and does not compromise miticidal efficacy of the composition. Verification of the pH of the mixture and adjustment with a solution of a buffer or neutralizing agent, and also the incorporation of the optional additives, may be carried out, according to their chemical nature, during one of the steps of the method of preparation. In some embodiments, the spinosyn composition includes one or more dermatologically and/or ophthalmically acceptable pH adjusting agents or buffering agents, including, but not limited to, acids such as acetic, boric, citric, lactic, phosphoric and hydrochloric acids; bases such as sodium hydroxide, sodium phosphate, sodium borate, sodium citrate, sodium acetate, sodium, lactate and tris-hydroxymethylaminomethane; and buffers such as citrate/dextrose, sodium bicarbonate and ammonium chloride. Such acids, bases and buffers are included in an amount required to maintain pH of the composition in a dermatologically and/or ophthalmically acceptable range.

In some embodiments, the composition comprises no additional agent that has activity against the *Demodex* mite. In some embodiments, the composition includes no active agent other than the one or more spinosyn compounds.

In some embodiments, where possible, the composition may include pharmaceutically acceptable salts of compounds in the composition, such as spinosyn compounds and other compounds when present. In some embodiments, the composition comprises acid addition salts of the compound (s). In some embodiments, the composition comprises base addition salts of the compounds(s). As used herein, the term pharmaceutically acceptable salts or complexes refers to salts or complexes (e.g., solvates, polymorphs) that retain the desired biological activity of the parent compound and exhibit minimal, if any, undesired toxicological effects.

In some embodiments, the composition further comprises an additional agent having miticidal activity against the *Demodex* mite, such as one or more agents selected from among ivermectin, pyrethrin, pyrethroid (e.g., permethrin, resmethrin, or D-phenothrin), tea tree oil (TTO), TTO component (e.g., terpinen-4-ol (T4O)), metronidazole, hypochlorous acid (HOCl), essential oil (e.g., peppermint oil or *Salvia*), alkali metal salt (e.g., lithium salt), phosphorothioate (e.g., a non-volatile, fat soluble phosphorothioate such as coumaphos), or formamidine (e.g., amitraz).

In some embodiments, the composition further comprises one or more antibiotic agents. In some embodiments, the antibiotic agent has antibacterial activity against one or more bacteria found on or within the *Demodex* mite, such as *Streptococci, Staphylococci*, or *Bacillus oleronius*. In some embodiments, the antibiotic agent also has miticidal activity, such as metronidazole.

In some embodiments, the composition further comprises one or more anti-inflammatory agents. Examples of anti-inflammatory agents that may be included are glucocorticoid or other steroid (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drug (e.g., salicylates, arylalkanoic acids, 2-arylpropionic acids, N-arylanthranilic acids, oxicams, coxibs, or sulphonanilides), Cox-2-specific inhibitor (e.g., valdecoxib, celecoxib, or rofecoxib), leflunomide, gold thioglucose, gold thiomalate, aurofin, sulfasalazine, hydroxychloroquinine, minocycline, TNF-alpha binding protein (e.g., infliximab, etanercept, or adalimumab), abatacept, anakinra, interferon-beta, interferon-gamma, interleukin-2, allergy vaccine, antihistamine, antileukotriene, beta-agonists, theophylline, or anticholinergic, antibiotics, tacrolimus, or retinoid.

In some embodiments, the anti-inflammatory agent is formulated for topical use. In some embodiments, the topical anti-inflammatory agent is a topical steroid. In the U.S., topical steroids are classified (Class/Group I-VII) by their ability to constrict capillaries and cause skin blanching, with Group I being the strongest or most potent, and Group VII being the weakest and mildest. Some examples of topically formulated steroids that may be utilized include clobetasol, betamethasone, diflorasone, fluocinonide, flurandrenolide, halobetasole, amcinonide, desoximetasone, halcinonide, fluticasone, triamcinolone, fluocinolone, hydrocortisone, mometasone, triamcinolone, alclometasone, denoside, and prednicarbate.

In some embodiments, the anti-inflammatory agent is formulated for ophthalmic use. Some examples of ophthalmically formulated steroids that may be utilized include dexamethasone, difluprednate, fluoromet, loteprednol etabonate, and rimexolone.

Optionally, the composition may include an abrasive agent for administration to areas of skin and hair adjacent to the eye. Inclusion of the abrasive may serve to mechanically agitate an area of tissue adjacent the eye, eyelid, eyelash, and follicle to improve access of the one or more spinosyn compounds in the composition to the *Demodex*. The treatment may work to agitate or move unwanted material such as *Demodex* eggs, larva or mites and remove them from the eyelash follicle or other part of the eye or eyelid, or to make them accessible to the spinosyn composition. The abrasive may also eliminate organisms by direct killing or damage. The abrasive may include any abrasive particle, powder, or crystal including but not limited to one or more of the following: aluminum oxide (e.g., alumina, aluminum trioxide, corundum powder), barium sulfate, boron nitride, calcium carbonate, cellulose acetate, ceramic, diamond, diatomaceous earth, emerald, ethylene/acric acid copolymer, fibers, garnet, glass, kaolin, lauroyl lysine, lava, magnesium oxide, mica, modified starch, nylon, other metals, other polymers, other silicon dioxides or silicon containing materials, polyethylene, polymethyl methacrylate polypropylene, polystyrene, polytetrafluoroethylene (PTFE), pumice, ruby, sand, sapphire, seashells, sericite, silica, silicon dioxide, silicon carbide, sodium bicarbonate, sodium chloride crystals, starch, silk, talc, topaz, zeolite, or polymer particles.

An abrasive particle may be any shape and have any number of sides. An abrasive particle may be overall diamond (triangle) shaped, elliptical, marquise shaped, octagonal, oval, pear shaped, rectangular, round, squared, or may be combinations or variations (e.g., a rounded square) of these shapes. An abrasive particle may have one surface or may have more than one surface (e.g., sides or faces). An abrasive particle may have 2, 3, 4, 5, 6-10, 11 to 20, 21 to 30, up to 40, up to 50, up to 60, or more than 60 sides. A surface of an abrasive particle may be substantially smooth, regular, textured or irregular. An abrasive particle may have one or more sharp edges or points. An abrasive particle may be sized from about 1 to about 600 microns across a longest dimension.

Abrasive particles in a group may all be similarly shaped to one another or may be differently shaped from one another. Abrasive particles in a group may all be about the same size, or may range in size. A group of particles may be larger than a minimum or may be smaller than a maximum. A group of abrasive particle may include particles from about 1 to about 15 microns across, about 15 microns to about 25 microns, about 25 microns to about 100 microns, about 100 to about 300 microns, or about 300 to about 600 microns. In one example, a group of abrasive particles may include particles from greater than about 25 microns to less than about 300 microns across. Differently sized and differently shaped particles may be chosen for different reasons. Different sizes and shapes may be chosen for different eye area conditions, different skin types or sensitivities, and/or different methods of application. A particle with a rough surface may be applied using an applicator, such as a wand or towelette, while a substantially round particle may be propelled towards the surface under pressure.

An abrasive may include a group of separate particles, or may include a substrate with an abrasive surface or may be any combination or variation. A substrate may have a plurality of abrasive particles connected with (attached to) it to provide an abrasive surface, or it may be a material having a rough textured surface. A rough textured surface may have a pore size on its surface from about 1 to about 15 microns across, about 15 microns to about 25 microns, about 25 microns to about 100 microns, about 100 to about 300 microns, or about 300 to about 600 microns.

Ointments

In some embodiments, a dermatologically and/or ophthalmically acceptable base includes a pharmaceutically acceptable ointment base. Examples of suitable ointment bases include, but are not limited to, oleaginous ointment bases such as petrolatum (e.g., liquid petrolatum or white petrolatum), plastibase, hard paraffin, white soft paraffin, yellow soft paraffin, liquid paraffin, emulsifying wax, microcrystalline wax, white bees wax, yellow bees wax, carnauba wax, wool wax (wool fat), mineral oil, olive oil, purified lanolin, anhydrous lanolin, and water soluble ointment bases such as polyethylene glycol (e.g., polyethylene glycol 400 or polyethylene glycol 3350), propylene glycol, polyoxyethylene, polyoxypropylene, or any combinations thereof.

In some embodiments, the composition is an ointment and includes one or more excipients selected from among petrolatum, mineral oil, propylparaben, methylparaben, lanolin, chlorobutanol, water, lanolin alcohol, sodium thiosulfate, sodium phosphate monobasic, phenylmercuric acetate, mannitol, zinc chloride, sodium phosphate, potassium acetate, hypromelloses, gentamcicin sulfate, boric acid, sodium hydroxide, lanolin oil, carbomer homopolymer type B (allyl pentaerythritol crosslinked), or benzalkonium chloride.

In some embodiments, the spinosyn composition is an ointment having a petrolatum base. Petrolatum is a semisolid mixture of hydrocarbons that provides certain advantages for skin and ophthalmic applications. Petrolatum is a pseudoplastic, which provides solid state behavior, which increases stability and prevents phase separation and settling of suspended particles. Petrolatum is thixotropic, which is excellent for retaining a drug in suspension while retaining spreadability. For ophthalmic uses, this permits spreading in the eye and as shear force is applied (when blinking), the product becomes more fluid and retains fluidity, helping to coat the eye. Because petrolatum is non-aqueous, it spreads and softens but will not be flushed out of the eye with tears (unlike aqueous solutions). As an non-aqueous and non-hygroscopic excipient, issues with hydrolysis and hydrolytic degradation of components can be avoided. As an insoluble excipient, petrolatum limits the treatment to local delivery, with little if any system absorption. Petrolatums for pharmaceutical products are classified as Petrolatum USP and White Petrolatum USP. For ophthlmic uses, while petrolatums are typically preferred. Petrolatums vary in color and clarity, as well as rheological properties (consistency, flow, and yield stress). Additional excipients such as mineral oil, surfactants, and preservatives can lower the apparent viscosity and yield stress relative to their concentration in the formulation.

Emulsions

The compositions of the invention may be formulated as an emulsion, e.g., an oil-in-water emulsion. The topical oil-in-water emulsion compositions may be in liquid, paste, or solid form, or in the form of ointments, creams, gels, sprays, foams, suspensions, lotions, shampoos, or washing bases. The compositions may also be in the form of suspensions of microspheres or nanospheres or of lipid or polymeric vesicles or of polymeric patches and of hydrogels for controlled release. These compositions for topical application may be in anhydrous form, in aqueous form or in the form of an emulsion.

In some embodiments of the invention, the composition is in the form of an emulsion of the cream or lotion type, of a gel, or of a solution, and more particularly in the form of a cream.

In some embodiments, the emulsion includes one or more excipients selected from among water, sodium hydroxide, polysorbate 80, glycerine, castor oil, carbomer copolymer type A, sodium acetate, boric acid, sorbic acid, edetate disodium, or silicone oil or silicone polymer gel (e.g., dimethicone or cyclomethicone).

Conventional emulsions are typically relatively unstable, virtually homogeneous systems of two immiscible liquids, one of which is dispersed in the other in the form of fine droplets (micelles). This dispersion is stabilized by virtue of the action of surfactant-emulsifiers which modify the structure and the ratio of the forces at the interface, and therefore increase the stability of the dispersion by decreasing the interface tension energy. Surfactant emulsifiers are amphiphilic compounds possessing a hydrophobic component having affinity for oil and a hydrophilic component having affinity for water, thus creating a link between the two phases. Ionic or nonionic emulsifiers therefore stabilize oil/water emulsions by adsorbing to the interface and forming lamellar layers of liquid crystals.

The compositions of the invention may contain one or more non-ionic surfactant emulsifiers. The emulsifier power of non-ionic surfactants is closely linked to the polarity of the molecule. This polarity is defined by the HLB (hydrophilic/lipophilic balance). Conventional emulsions are generally stabilized by a mixture of surfactants, the HLBs of which can be quite different but the proportion of which in the mixture corresponds to the required HLB of the fatty phase to be emulsified.

Suitable non-ionic surfactant emulsifiers can be selected from the group consisting of Cetostearyl alcohol, Cetyl alcohol, Cocamide DEA, Cocamide MEA, Isoceteth-20, Oleyl alcohol, Sorbitan monostearate, Sorbitan tristearate, Stearyl alcohol, tyloxapol, softigen, solutol HS15, poloxamers such as Pluronic F-68LF™ or Lutrol F68, Pluronic L-62LF™ and Pluronic L62D™ (BASF Wyandotte Corp., Parsippany, N.J., USA), polysorbates such as polysorbate 20 and polysorbate 80, polyoxyethylene fatty acid esters such as Emulphor™ (GAF Corp., Wayne, N.J., USA).

In some embodiments, the emulsion includes a carbomer homopolymer (Carbopol), which can emulsify oil-in-water type suspensions, allowing for non-cloudy/non-sticky formulations.

In some embodiments, the compositions of the invention are oil-in-water emulsions that comprise: (a) one or more spinosyn compounds; (b) an oily phase comprising a fatty substance and/or an emollient; (c) water; and, optionally, (d) a surfactant emulsifier.

Examples of fatty substances include vegetable, mineral, animal or synthetic oils, silicone oils, Guerbet alcohols or other substances, and mixtures thereof.

Examples of mineral oils include paraffin oils of various viscosities, such as Primol 352, Marcol 82 or Marcol 152 marketed by Esso. Examples of vegetable oil include sweet almond oil, palm oil, soybean oil, sesame oil and sunflower oil. Examples of animal oils include lanolin oil, squalene oil, fish oil, and mink oil. Examples of synthetic oils include esters, such as cetearyl isononanoate marketed in particular under the name Cetiol SN by Cognis France, diisopropyl adipate, for instance, the product marketed under the name Ceraphyl 230 by ISF, isopropyl palmitate, for instance the product marketed under the name Crodamol IPP by Croda, or caprylic capric triglyceride such as Miglyol 812 marketed by Huls/Lambert Riviere. Examples of silicone oils include dimethicone, such as the product marketed under the name Dow Corning 200 fluid, and cyclomethicone, such as the product marketed under the name Dow Corning 244 fluid by Dow Corning, and the product marketed under the name Mirasil CM5 by SACI-CFPA.

Other fatty substances may include fatty acids such as white petrolatum, stearic acid, fatty alcohols such as stearyl alcohol, cetostearyl alcohol and cetyl alcohol, or derivatives thereof, waxes such as beeswax, carnauba wax or candelilla wax, and also gums, in particular silicone gums.

One or more fatty substances in the composition may be present in an amount of about 20% to about 40% by weight of the composition. In some embodiments, the one or more fatty substances are present in an amount of about 20% to about 35% by weight of the composition.

The oily phase of the composition can include one or more emollients, such as vegetable, mineral, animal or synthetic oils, silicone oils, isopropyl palmitate, 1-decene polymer (hydrogenated), $C_{12}$-$C_{15}$ alkyl benzoate, $C_{12}$-$C_{15}$ alkyl benzoates esters, lanolin alcohol and isopropyl myristate; and mixtures thereof. Emollients in the composition may be present in an amount of about 10% to about 20% by weight of the composition.

In some embodiments, the oily phase of the composition comprises a mixture of fatty substances and emollients, and in some embodiments, at least two emollients. In some embodiments, the fatty substances are white petrolatum and mineral oil and the emollients are lanolin alcohol and isopropyl myristate.

The oily phase of the emulsion may be present at a content of from 15 to 45% by weight relative to the total weight of the composition, and preferably from 20 to 40% by weight.

The composition may comprise up to 15% by weight of a suitable surfactant emulsifier. In some embodiments, the surfactant emulsifier is present in the composition in from about 5% to about 15% by weight of the composition.

The composition may comprise from 0.1% to 10% of one or more spinosyns by weight relative to the total weight of the composition. In some embodiments, the composition comprises from 0.5% to 10% of one or more spinosyns by weight relative to the total weight of the composition.

The composition of the invention may also contain water or buffer ranging from 50% to 95%. In some embodiments, the composition contains from 55% to 80% water or buffer by weight relative to the total weight of the composition. The water used in the composition according to the invention is preferably purified or distilled water.

The composition may also contain inert additives or combinations of additives, such as flavor enhancers; preservatives; stabilizers; humidity regulators; pH regulators; osmotic pressure modifiers; UV-A and UV-B screening agents; and antioxidants. In some embodiments, the oil-in-water emulsion composition of spinosyn is devoid of preserving agents.

These additives may be present in the composition at a concentration from 0.001% to 20% by weight relative to the total weight of the composition.

In some embodiments, the compositions are oil-in-water emulsions that comprise: (a) one or more spinosyns in an amount of about 0.01% to about 10% by weight; (b) an oily phase comprising one or more fatty substances in an amount of about 20% to about 40% by weight and one or more emollients in an amount of about 10% to about 20% by weight; (c) one or more surfactant emulsifiers in an amount of about 5% to about 15% by weight; and (d) water.

Exemplified Formulations of the Composition

In some embodiments, the composition is a cream, wherein in addition to the one or more spinosyn compounds (e.g., spinosad), the composition includes one or more of the following ingredients: water or buffer, mineral oil, acetylated lanolin alcohol, stearyl alcohol, cetearyl alcohol, and propylene glycol. In some embodiments, the cream includes each of the foregoing ingredients.

In some embodiments, the composition is a cream, wherein in addition to the one or more spinosyn compounds (e.g., spinosad), the composition includes one or more of the following ingredients: water or buffer, propylene glycol, mineral oil, actylated lanolin alcohol, cetyl alcohol, stearyl alcohol, cetearyl alcohol, and polyoxyl 35 castor oil. In some embodiments, the cream includes each of the foregoing ingredients.

In some embodiments, the composition is a lotion, wherein in addition to the one or more spinosyn compounds (e.g., spinosad), the composition includes one or more of the following ingredients: water or buffer, isopropyl myristate, castor oil, polyoxyl 40 stearate, cetearyl alcohol, and cetyl esters wax. In some embodiments, the lotion includes each of the foregoing ingredients.

In some embodiments, the composition is an ointment, wherein in addition to the one or more spinosyn compounds (e.g., spinosad), the composition includes one or more of the following ingredients: water or buffer, propylene glycol, castor oil, acetylated lanolin alcohol, cetyl alcohol, stearyl alcohol, cetearyl alcohol, cetyl esters wax, povidone K 90, and stearic acid. In some embodiments, the ointment includes each of the foregoing ingredients.

In some embodiments, the composition is an ointment, wherein in addition to the one or more spinosyn compounds (e.g., spinosad), the composition includes one or more of the following ingredients: propylene glycol, mineral oil, acetylated lanolin alcohol, stearyl alcohol, glyceryl stearate/PEG-100 stearate, polyoxyl 40 stearate, and stearic acid. In some embodiments, the ointment includes each of the foregoing ingredients.

In some embodiments, the composition is one described by one of Tables 1-5. In some embodiments, for a given composition, the sum of each % concentration of the listed ingredients in the table is 100%.

In some embodiments, the composition is one described by one of Tables 1-5, but with one or more of the listed excipients substituted for one or more different excipients having the same listed function(s).

In some embodiments, in each of Tables 1-5, using 0.1% spinosad as a reference point, for each incremental w:w % decrease of spinosad concentration, the same incremental w:w % increase is made to the ingredient that is dominant in the formulation (i.e., the ingredient having the greatest minimum %). Conversely, for each incremental w:w % increase of spinosad, there is a decrease by the same w:w % from the excipient that is dominant in the formulation. As an example, in Table 1, for each 0.1% increase in spinosad from 0.1% spinosad, there would be a corresponding decrease of 0.1% in distilled water or buffer. As a further example, in Table 5, for each 1.0% increase in spinosad from 0.1%, there would be a corresponding decrease of 1% in mineral oil.

TABLE 1

Creams

| Active/Excipient | Function | Range (w:v %) |
| --- | --- | --- |
| Spinosad | Active | 0.1%-10% |
| Distilled Water or buffer | Solvent, pH adjuster, vehicle part of the cream base | 54-90 |
| Mineral oil | Emollient, moisturizer, solvent | 15-97 |
| Acetylated lanolin alcohol | Solubilizer and emulsifier | 5-8 |
| Cetyl esters wax | Thickener and emollient | 10-10.3 |
| Stearyl alcohol | emulsion stabilizer, surfactant/emulsifying agent, viscosity increasing agent. | 5-15 |
| Cetearyl alcohol | Emulsifier and thickener | 7-8 |
| Propylene glycol | Solvent | 3-71 |

TABLE 2

Creams

| Active/Excipient | Function | Range (w:v %) |
| --- | --- | --- |
| Spinosad | Active | 0.1-10% |
| Distilled Water or buffer | Solvent, pH adjuster, vehicle part of the cream base | 35-90 |
| Propylene glycol | solvent | 15-71 |
| Mineral oil | Emollient, moisturizer, solvent | 14-97 |
| Acetylated lanolin alcohol | Solubilizer and emulsifier | 6-8 |
| Cetyl alcohol | Emulsifier, thickener | 8-12 |

TABLE 2-continued

Creams

| Active/Excipient | Function | Range (w:v %) |
| --- | --- | --- |
| Stearyl Alcohol | emulsion stabilizer, surfactant/emulsifying agent, viscosity increasing agent. | 11-15 |
| Cetearyl alcohol | Emulsifier, solubilizer, thickener | 7-8 |
| Polyoxyl 35 castor oil | Surfactant, emulsifying agent, solubilizing agent | 4-4.86 |

TABLE 3

Lotions

| Active/Excipient | Function | Range (w:v %) |
| --- | --- | --- |
| Spinosad | Active | 0.1-10% |
| Distilled Water or buffer | Solvent, pH adjuster, vehicle part of the cream base | 70-90 |
| Isopropyl myristate | solvent | 3-15 |
| Castor oil | Solvent, vehicle, skin softener | 10-15 |
| Polyoxyl 40 stearate | Solubilizer and emulsifier | 2-8.8 |
| Cetearyl alcohol | Emulsifier, solubilizer, thickener | 4-8 |
| Cetyl esters wax | Thickener and emollient | 10-10.3 |

TABLE 4

Ointments

| Active/Excipient | Function | Range (w:v %) |
| --- | --- | --- |
| Spinosad | Active | 0.1-10% |
| Distilled Water or buffer | Solvent, pH adjuster, vehicle part of the cream base | 13-90 |
| Propylene glycol | solvent | 30-71 |
| Castor oil | Emollient, moisturizer, solvent | 15-97 |
| Acetylated lanolin alcohol | Solubilizer and emulsifier | 5-8 |
| Cetyl alcohol | Emulsifier, thickener | 10-12 |
| Stearyl Alcohol | emulsion stabilizer, surfactant/emulsifying agent, viscosity increasing agent. | 10-15 |
| Cetearyl alcohol | Emulsifier, solubilizer, thickener | 5-8 |
| Cetyl esters wax | Thickener and emollient | 5-10.3 |
| Povidone K 90 | Thickener, gelling polymer | 1-2 |
| Stearic acid | Surfactant, emulsifying agent, thickener | 5-22.5 |

TABLE 5

Ointments

| Active/Excipient | Function | Range (w:v %) |
| --- | --- | --- |
| Spinosad | Active | 0.1-10% |
| Propylene glycol | solvent | 32-71 |
| Mineral oil | Emollient, moisturizer, solvent | 44-97 |
| Acetylated lanolin alcohol | Solubilizer and emulsifier | 5-8 |
| Stearyl Alcohol | emulsion stabilizer, surfactant/emulsifying agent, viscosity increasing agent. | 8-15 |

TABLE 5-continued

| Ointments | | |
|---|---|---|
| Active/Excipient | Function | Range (w:v %) |
| Glyceryl stearate/PEG-100 stearate | Emulsifier, solubilizer | 3-7.5 |
| Polyoxyl 40 stearate | Solubilizer and emulsifying agent | 2-8.8 |
| Stearic acid | Surfactant, emulsifying agent, thickener | 5-22.5 |

Methods of Treatment

An aspect of the invention is a method for treating an ocular *Demodex* mite infestation of an eye of a human or animal subject, or for treating a condition of the eye or skin associated with ocular *Demodex* mite infestation, comprising topically administering a composition comprising one or more spinosyn compounds to the ocular surface (conjunctiva and/or cornea) or other anatomical structure of the eye, or to an area adjacent the eye.

Without being limited by theory as to potential mechanism of action, for an existing *Demodex* infestation, the goal of treatment as a therapy is typically to reduce the number of *Demodex* mites in an anatomical locus such as the ocular surface (conjunctiva and/or cornea) or other anatomical structure of the eye, or to an area adjacent the eye, so that any one or more signs of a *Demodex*-associated condition will be alleviated or eliminated. As *Demodex* mites represent a part of the normal skin microbiome, and the level of sensitivity to the *Demodex* mites and immunoreactive factors associated with the mites, may vary between subjects, the goal of therapy may be to reduce the number of living *Demodex* mites to a level that is normal or is healthy for that individual (below a threshold of parasitic over-population), or to eradicate all *Demodex* mites from the anatomical locus or loci targeted.

The composition may also be topically administered prophylactically to a subject without a *Demodex* infestation in order to prevent or delay onset of a *Demodex* infestation.

Through one or more administrations, an amount of a spinosyn compound that is sufficient to reduce the number of *Demodex* mites in a anatomical locus, as compared to a corresponding anatomical locus in the absence of the amount or concentration of the spinosyn or other miticide, is delivered (a miticidally effective amount).

The composition is to be topically administered to the ocular surface (conjunctiva and/or cornea) or other anatomical structure of the eye, or to an area adjacent the eye, which may be done by the subject (i.e., self-administered) or by another individual.

In some embodiments, for formulations intended for administration to the ocular surface, depending on its viscosity, the composition may be administered dropwise (e.g., as with an eye dropper), or placed at the corner of the eye or eyelid, or onto the inside of the upper or lower eyelid. For example, one or more drops (of, for example, about 30 microliters each) may be administered. The subject may blink to facilitate distribution of the composition on the ocular surface. In some embodiments, the composition is topically administered to the ocular surface, In some embodiments, the composition is topically administered to the ocular surface, or other anatomical structure of the eye, or to an area adjacent the eye, immediately before going to sleep.

In some embodiments, the composition is topically administered to an area adjacent to the eye, wherein the area comprises a sebaceous gland opening of the eyelid (e.g., one or more of gland of Zeis, gland of Moll, or Meibomian gland).

In some embodiments, the composition is topically administered to one or more structures of epidermal invaginations known as pilosebaceous units (e.g., hair, hair follicle, sebaceous gland).

The composition may be topically administered using an ocular or facial applicator, such as those described herein, or using a part of the body, such as a finger or knuckle (by wiping, rubbing, massaging, etc.).

Examples of applicators include a swab, cosmetic pad, wipe, wipe stick, towelette, sponge, gauze, puff, wand, brush, or comb. In some embodiments, the applicator includes at least a portion that makes contact with the target anatomical area and may be composed of woven or non-woven materials such as cotton, polyester, or rayon. Applicators may be disposable or reusable.

The spinosyn composition may be administered topically by gentle application to one or more anatomical sites on a subject, including the subject's ocular surface or other anatomical structure of the eye, or to an area adjacent to the eye such as an eyelid, eyelid margin, eyelashes, eyelash follicles, eyebrow, or eyebrow follicles, or to a sebaceous gland opening of the eyelid (e.g., one or more of gland of Zeis, gland of Moll, or Meibomian gland). The spinosyn composition may be massaged onto the skin. In some embodiments, the spinosyn composition is left on the area until the next treatment. In other embodiments, excess spinosyn composition is wiped away or washed away after administration.

Optionally, one or more anti-inflammatory agents may be administered to the subject before, during, or after administration of the spinosyn composition, which can assist in suppressing or reducing inflammation that may be caused by some embodiments of the spinosyn composition or by any mechanical irritation that may be applied as part of treatment. An anti-inflammatory agent may also suppress or reduce potential inflammation associated with the decaying mites. Anti-inflammatory agents may be administered to the subject by a route appropriate to the formulation. For example, an anti-inflammatory agent may be administered topically, included in the spinosyn composition or topically administered in a separate composition. In other embodiments, an anti-inflammatory agent may be administered to the subject systemically (e.g., orally).

Examples of anti-inflammatory agents that may be administered include a glucocorticoid or other steroid (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drug (e.g., salicylates, arylalkanoic acids, 2-arylpropionic acids, N-arylanthranilic acids, oxicams, coxibs, or sulphonanilides), Cox-2-specific inhibitor (e.g., valdecoxib, celecoxib, or rofecoxib), leflunomide, gold thioglucose, gold thiomalate, aurofin, sulfasalazine, hydroxychloroquinine, minocycline, TNF-alpha binding protein (e.g., infliximab, etanercept, or adalimumab), abatacept, anakinra, interferon-beta, interferon-gamma, interleukin-2, allergy vaccine, antihistamine, antileukotriene, beta-agonists, theophylline, or anticholinergic, antibiotics, tacrolimus, or retinoid.

Optionally, the anatomical site may be scrubbed prior to treatment with the spinosyn composition, as a pre-treatment or preparatory step, with an agent such as a cleansing substance. An abrasive may be applied to areas adjacent to the eye to remove skin, a layer of skin, skin debris, microorganisms, eyelashes, oils, and/or other related or unrelated substances. The abrasive may mechanically agitate area of tissue adjacent the eye, eyelid, eyelash, and follicle to improve access of the spinosyn composition to the *Demodex*. The treatment may work to agitate or move unwanted material such as *Demodex* eggs, larva or mites and remove them from the eyelash follicle or other part of the eye or eyelid, or to make them accessible to the spinosyn composition. The dermabrasive may also eliminate organisms by direct killing or damage. The abrasive may include any abrasive particle, powder, or crystal including but not limited to one or more of the following: aluminum oxide (e.g., alumina, aluminum trioxide, corundum powder), barium sulfate, boron nitride, calcium carbonate, cellulose acetate, ceramic, diamond, diatomaceous earth, emerald, ethylene/acric acid copolymer, fibers, garnet, glass, kaolin, lauroyl lysine, lava, magnesium oxide, mica, modified starch, nylon, other metals, other polymers, other silicon dioxides or silicon containing materials, polyethylene, polymethyl methacrylate polypropylene, polystyrene, polytetrafluoroethylene (PTFE), pumice, ruby, sand, sapphire, seashells, sericite, silica, silicon dioxide, silicon carbide, sodium bicarbonate, sodium chloride crystals, starch, silk, talc, topaz, zeolite, or polymer particles.

Optionally, before, during, or after administration of the spinosyn composition, an additional agent with activity against *Demodex* may be administered. In some embodiments, the agent has activity against *Demodex*, such as ivermectin, pyrethrin, pyrethroid (e.g., permethrin, resmethrin, or D-phenothrin), tea tree oil (TTO), TTO component (e.g., terpinen-4-ol (T4O)), metronidazole, hypochlorous acid (HOCl), essential oil (e.g., peppermint oil or *Salvia*), alkali metal salt (e.g., lithium salt), phosphorothioate (e.g., a non-volatile, fat soluble phosphorothioate such as coumaphos, also identified as O,O-Diethyl O-3-chloro-4-methyl-2-oxo-2H-chromen-7-yl phosphorothioate), or formamidine (e.g., amitraz, also identified as N,N'-[(Methylimino)dimethylidyne]di-2,4-xylidine). The additional agent may be administered as a component of the spinosyn composition, or administered in a separate composition, topically or by another route.

The dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

Detection of *Demodex*

The methods of the invention may further comprise confirming the presence of *Demodex* mites on the subject prior to administering the spinosyn composition to the subject. Several clinical signs can alert one to the presence of *Demodex* in the lashes. Appreciation of these clues can lead one to perform one of two simple examination techniques that will confirm the presence of the mites.

1. Cylindrical dandruff (CD). This is the most obvious clinical sign and an excellent indicator for mite infestation. Cylindrical dandruff is visible at the slit lamp, and it is different than the scaly, scurf-like debris seen with traditional anterior blepharitis.

2. Alterations of the skin surrounding the lash follicle. The skin near the opening of the follicle becomes distended and raised, possibly with a greasy, oily appearance to the skin surrounding the follicle.

3. Changes in lash appearance. In longstanding infestations, the lashes become thin and brittle, or they may begin to lose their color. Misdirection and loss of lashes may also occur.

4. Lid hyperemia/telangiectasia. Because the presence of mites is associated with increases in interleukins and different types of pro-inflammatory cytokines, increases in levels of lid inflammation may be apparent, which may lead to increased vascularization along the lid margin.

5. Patient history/associations with other disease. Prevalence of *Demodex* increases with age, and a strong association in patients with acne rosacea, seborrheic dermatitis, and other forms of inflammatory skin conditions has been observed, including allergic symptoms such as itching.

These clinical signs can alert to the presence of *Demodex* overpopulation. However, each of these items is not diagnostic in its own right—with the possible exception of cylindrical dandruff. Confirmation of the presence of mites, as well as a method of categorizing the degree of mite infestation can be done through one of two simple steps: lash epilation (e.g., two to four different lashes from the lid along with associated debris/cylindrical dandruff, viewing the complex under a light microscope) and lash rotation (transferring debris from the follicle to a slide and examining under a light microscope or visualizing under high magnification at a slit lamp (25-40×).

Accordingly, the presence of *Demodex* mites may be confirmed by one or more techniques, such as direct mite identification and measurement of mite density, e.g., presence of cylindrical dandruff at eyelash root, skin alteration surrounding lash follicle, changes in lashes, and lash sampling (ash epilation with light microscope or lash rotation with slit lamp). In addition to ex vivo depilation and microscopy, in vivo confocal microscopy may be used (Randon M et al., "In vivo confocal microscopy as a novel and reliable tool for the diagnosis of *Demodex* eyelid infestation," *Br J Ophthalmol*, 2015, 99(3):336-341, which is incorporated herein by reference in its entirety).

Molecular diagnostic techniques may be used to detect *Demodex*-associated molecules at the genetic level and/or protein level in biological samples taken from the subject from areas where the mites can be found (e.g., eyelashes, skin surface biopsies). For example, polymerase chain reaction (PCR) or immunoassay (e.g., enzyme-linked immunosorbent assay (ELISA)) may be used to detect and quantify target *Demodex* nucleic acid or protein molecules in skin and/or hair samples from the subject, such as exoskeletal chitin, chitin synthase, 62-kDa and 83-kDa antigen of *Bacillus oleronius* (see, for example, Zhao Ya-e et al., "Cloning and sequence analysis of chitin synthase gene fragments of *Demodex* mites," *J Zheijang Univ Sci B*, 2012, 13(10):763-768; Zhao Ya-e et al., "Discrimination between *Demodex folliculorum* (Acari: Demodicidae) isolates from China and Spain based on mitochondrial cox1 sequences," *J Zheijang Univ Sci B*, 2013, 14(9):829-836; Hu L et al., "Molecular identification of four phenotypes of human *Demodex* in China," *Exp Parisitol*, 2014, 142:38-42; Li J et al., "Correlation between ocular *Demodex* infestation and serum immunoreactivity to *Bacillus* proteins in patients with facial rosacea," *Ophthalmology*, 2010, 117(5):870-877; Szkaradkiewicz A et al., "*Bacillus oleronius* and *Demodex* mite infestation in patients with chronic blepharitis," *Clinical Microbiology and Infection*, 2012, 18(10):1020-1025; Kasetsuwan N et al., "Prevalence of ocular demodicosis among patients at Tertiary Care Center, Bangkok, Thailand," *Int J Ophthalmol*, 2017, 10(1):122-127; Liu D et al., "*Demodex* (Hair Follicle Mite)", Chapter 72 in Molecular Detection of Human Parasitic Pathogens, CRC Press, 2012, pages 741-750, which are each incorporated herein by reference in their entirety).

Thus, in some embodiments of the methods of the invention, confirmation of the presence of *Demodex* mites comprises identifying the *Demodex* mites in vivo or in a biological sample (e.g., a hair or skin sample) ex vivo, or detecting a molecule associated with *Demodex* mites (e.g., chitin, chitin synthase, lipase. *Demodex*-associated bacterial antigen (e.g., *Bacillus* antigen such as *B. oleronius* antigen), *Demodex* 16S rDNA, *Demodex* 18S rDNA). For example, *Demodex* mites have been shown to produce immune-reactive lipase, which may be used as a target for detection of the mite (Jimenez-Acosta F. et al., "*Demodex* mites contain immuno reactive lipase," *Arch Dermatol.*, 1989, 125:1436-7). Target DNA and RNA may be extracted and amplified and used qualitatively as molecular barcodes for identification and inter-species and intra-species differentiation, and used quantitatively to assess extent of infestation. Gene or protein microarray-based analysis may also be utilized. Biological samples from the subject such as skin surface, hair, tears, and peripheral blood may be analyzed for the presence and levels of inflammatory markers that are consistent with *Demodex* infestation.

To monitor the progress of a treatment or to confirm its efficacy, the presence or absence of *Demodex* mites or a threshold amount of *Demodex* mites on a subject may be carried out on a subject-derived sample after a course of treatment for a period of time to determine whether the *Demodex* have been reduced to normal levels or been eradicated by the treatment.

The detection step may be used for any purpose for which detection of *Demodex* (e.g., *D. folliculorum* and/or *D. brevis*) is desirable, including diagnostic and prognostic applications, such as in laboratory and clinical settings. Appropriate samples include any biological samples in which *Demodex* may be found, including clinical samples obtained from a medical subject (human) or veterinary subject (non-human animal).

When the target molecule associated with *Demodex* mites within a sample is one that may be targeted by antibodies, such as a protein or carbohydrate (e.g., chitin, chitin synthase, lipase, *Demodex*-associated bacterial antigen (e.g., *Bacillus* antigen such as *B. oleronius* antigen), immuno-chemical techniques using antibodies, either polyclonal or monoclonal, or antigen-binding fragments of such antibodies, may be used. These immunochemical techniques can involve either radioimmunoassay or other well-established assay techniques, such enzyme-linked immunosorbent assay (ELISA). Target molecules can also be measured by standard non-immunochemical techniques such as gas chromatography.

Detecting a target nucleic acid in a sample (e.g., *D. folliculorum* and/or *D. brevis* nucleic acid, or *Demodex*-associated bacterial nucleic acid, or subject immune molecule) using genetic-based molecular diagnostic techniques typically involves contacting the sample with at least one probe that is capable of hybridizing to the target nucleic acid, such as a *D. folliculorum* and/or *D. brevis* nucleic acid, under conditions of very high stringency, and detecting hybridization between the target nucleic acid and the probe. Detection of hybridization between the probe and the target nucleic acid indicates the presence of the target nucleic acid (and thus, the organism, e.g., *D. folliculorum* and/or *D. brevis*) in the sample.

In some embodiments, *D. folliculorum* and/or *D. brevis* nucleic acids present in a sample are amplified prior to using a hybridization probe for detection. For instance, it can be advantageous to amplify a portion of the *D. folliculorum* and/or *D. brevis* nucleic acid, and then detect the presence of the amplified *D. folliculorum* and/or *D. brevis* nucleic acid.

Detecting the amplified product typically includes the use of labeled probes that are sufficiently complementary and hybridize to the amplified target nucleic acid sequence. Thus, the presence, amount, and/or identity of the amplified product can be detected by hybridizing a labeled probe, such as a fluorescently labeled probe, complementary to the amplified product. In one embodiment, the detection of a target nucleic acid sequence of interest, such as a *D. folliculorum* and/or *D. brevis* nucleic acid includes the combined use of PCR amplification and a labeled probe such that the product is measured using real-time PCR. In another embodiment, the detection of an amplified target nucleic acid sequence of interest includes the transfer of the amplified target nucleic acid to a solid support, such as a blot, for example a Northern blot, and probing the blot with a probe, for example a labeled probe, that is complementary to the amplified target nucleic acid sequence. In yet another embodiment, the detection of an amplified target nucleic acid sequence of interest includes the hybridization of a labeled amplified target nucleic acid to probes disclosed herein that are arrayed in a predetermined array with an addressable location and that are complementary to the amplified target nucleic acid.

Any nucleic acid amplification method can be used to detect the presence of *Demodex* in a sample. In one specific, non-limiting example, polymerase chain reaction (PCR) is used to amplify the target nucleic acid sequences. In other specific, non-limiting examples, real-time PCR, reverse transcriptase-polymerase chain reaction (RT-PCR), real-time reverse transcriptase-polymerase chain reaction (rt RT-PCR), ligase chain reaction, or transcription-mediated amplification (TMA) is used to amplify the target nucleic acid. In a specific example, the *D. folliculorum* and/or *D. brevis* nucleic acid is amplified by real-time PCR, for example real-time TAQMAN® PCR. Techniques for nucleic acid amplification are well-known to those of skill in the art.

Typically, at least two primers are utilized in the amplification reaction. Amplification of the *Demodex* nucleic acid involves contacting the *Demodex* nucleic acid with one or more primers that are capable of hybridizing to and directing the amplification of a *Demodex* nucleic acid (such as a primer capable of hybridizing under very high stringency conditions to *D. folliculorum* and/or *D. brevis*.

The amplified *Demodex* nucleic acid, can be detected in real-time, for example by real-time PCR, in order to determine the presence, and/or the amount of *Demodex*-specific nucleic acid (e.g., *D. folliculorum* and/or *D. brevis*) in a biological sample. In this manner, an amplified nucleic acid sequence, such as an amplified *D. folliculorum* and/or *D. brevis* nucleic acid sequence, can be detected using a probe specific for the product amplified from the *Demodex* sequence of interest.

A fluorophore is a chemical compound, which when excited by exposure to a particular stimulus such as a defined wavelength of light, emits light (fluoresces), for example at a different wavelength (such as a longer wavelength of light). Fluorophores are part of the larger class of luminescent compounds. Luminescent compounds include chemi-luminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

A probe comprises an isolated nucleic acid capable of hybridizing to a target nucleic acid (such as *Demodex* nucleic acid, for example *D. folliculorum* and/or *D. brevis* ribosomal nucleic acid molecule). A detectable label or reporter molecule can be attached to a probe. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al., Molecular Cloning: A Laboratory Manual, Cold Spring Harbor Laboratory Press (1989) and Ausubel et al., Current Protocols in Molecular Biology, Greene Publishing Associates and Wiley-Intersciences (1987).

One of ordinary skill in the art will know suitable methods for extracting nucleic acids such as RNA and/or DNA from a sample; such methods will depend upon, for example, the type of sample in which the *Demodex* nucleic acid is found. For example, the nucleic acids may be extracted using guanidinium isothiocyanate, such as the single-step isolation by acid guanidinium isothiocyanate-phenol-chloroform extraction of Chomczynski et al. (*Anal. Biochem.*, 1997, 162:156-59). The sample can be used directly or can be processed, such as by adding solvents, preservatives, buffers, or other compounds or substances. Nucleic acids can be extracted using standard methods. For instance, rapid nucleic acid preparation can be performed using a commercially available kit (such as the QIAGEN® DNA Mini kit (QIAGEN®) Roche MagNA Pure Compact Nucleic Acid Isolation Kit I or RNEASY® Mini Kit (QIAGEN®); NUCLISENS® NASBA Diagnostics (bioMerieux); or the MASTERPURE™ Complete DNA and RNA Purification Kit (EPICENTRE)).

An array may be used to rapidly detect *Demodex* nucleic acids in a sample. Arrays are arrangements of addressable locations on a substrate, with each address containing a nucleic acid, such as a probe, such as a *Demodex* probe. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

The use of the term "array" includes the arrays found in DNA microchip technology. As one, non-limiting example, the probes could be contained on a DNA microchip similar to the GENECHIP® products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. After fabrication, the array is ready for hybridization. The probe or the nucleic acid within the sample may be labeled, such as with a fluorescent label and, after hybridization, the hybridization signals may be detected and analyzed.

Combination Treatments

Additional agents can be administered to the subject simultaneously or consecutively with the spinosyn composition. Additional agents can be administered before, during, or after topical administration of the spinosyn composition. The additional agents may be administered within the same composition as the one or more spinosyn compounds, or administered to the subject in a separate composition. If administered in a separate composition, the additional agents may be administered topically or by any local or systemic route appropriate for the additional agents to have the desired effect on the subject. In some embodiments, the additional agent is administered topically. In other embodiments, the additional agent is administered orally.

In some embodiments, the additional agent is one having miticidal activity against the *Demodex* mite, such as one or more agents selected from among ivermectin, pyrethrin, pyrethroid (e.g., permethrin, resmethrin, or D-phenothrin), tea tree oil (TTO), TTO component (e.g., terpinen-4-ol (T4O)), metronidazole, hypochlorous acid (HOCl), essential oil (e.g., peppermint oil or *Salvia*), alkali metal salt (e.g., lithium salt), phosphorothioate (e.g., a non-volatile, fat soluble phosphorothioate such as coumaphos), or formamidine (e.g., amitraz, also identified as N,N'-[(Methylimino)dimethylidyne]di-2,4-xylidine).

Permethrin is a member of the pyrethroids, which are a class of synthetically derived insecticides. Pyrethroids are structurally related to naturally occurring pyrethrins, pyrethrin I and pyrethrin II. Synthetic pyrethroids include permethrin (U.S. Pat. No. 4,113,968; U.S. Patent Publication 20160361297), resmethrin, and sumithrin (U.S. Pat. Nos. 3,934,023 and 2,348,930), which are each incorporated by reference herein in their entirety. Other examples of pyrethroids include bifenthrin, cyfluthrin, cypermethrin, cyphenothrin, D-phenethrin, deltamethrin, esfenvalerate, etofenprox, fenprropathrin, flumethrin, gamma-cyhalothrin, imiprothrin, lambda-cyalothrin, momfluorothrin, permethrin, prallethrin, pyrethrin, tau-fluvalinate, tefluthrin, and tetramethrin.

In some embodiments, the additional agent is an antibiotic agent. In some embodiments, the antibiotic agent has antibacterial activity against one or more bacteria found on or within the *Demodex* mite, such as *Streptococci, Staphylococci*, or *Bacillus oleronius*. In some embodiments, the antibiotic agent also has miticidal activity, such as metronidazole.

In some embodiments, the additional agent is one or more anti-inflammatory agents. Examples of anti-inflammatory agents that may be included are glucocorticoid or other steroid (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drug (e.g., salicylates, arylalkanoic acids, 2-arylpropionic acids, N-arylanthranilic acids, oxicams, coxibs, or sulphonanilides), Cox-2-specific inhibitor (e.g., valdecoxib, celecoxib, or rofecoxib), leflunomide, gold thioglucose, gold thiomalate, aurofin, sulfasalazine, hydroxychloroquinine, minocycline, TNF-alpha binding protein (e.g., infliximab, etanercept, or adalimumab), abatacept, anakinra, interferon-beta, interferon-gamma, interleukin-2, allergy vaccine, antihistamine, antileukotriene, beta-agonists, theophylline, or anticholinergic, antibiotics, tacrolimus, or retinoid.

In some embodiments, the anti-inflammatory agent is formulated for topical use. In some embodiments, the topical anti-inflammatory agent is a topical steroid. In the U.S., topical steroids are classified (Class/Group I-VII) by their ability to constrict capillaries and cause skin blanching, with Group I being the strongest or most potent, and Group VII being the weakest and mildest. Some examples of topically formulated steroids that may be utilized include clobetasol, betamethasone, diflorasone, fluocinonide, flurandrenolide, halobetasole, amcinonide, desoximetasone, halcinonide, fluticasone, triamcinolone, fluocinolone, hydrocortisone, mometasone, triamcinolone, alclometasone, denoside, and prednicarbate.

In some embodiments, the anti-inflammatory agent is formulated for ophthalmic use. Some examples of ophthalmically formulated steroids that may be utilized include dexamethasone, difluprednate, fluorometholone, loteprednol etabonate, and rimexolone.

In some embodiments, the additional agent is one or more alkali metal salts, which may be used as a miticidal agent. Lithium salts are the preferred alkali metal salts. Lithium chloride is the most preferred alkali metal salt.

It should be understood that whenever a reference is made to alkali metal salts or lithium salts, such alkali metal salts or lithium salts comprise any organic as well as inorganic salts of alkali metals or lithium which are suitable for and capable of exerting a miticidal effect, preferably on the *Demodex* mite. Organic salts of alkali metals such as lithium include salts such as the citrate salt, carbonate salt, lactate salt, formate salt, acetate salt, trifluoroacetate salt, maleate salt, tartrate salt, orotate salt and the like. Inorganic acid salts of alkali metals include salts such as the fluoride salt, chloride salt, bromide salt, sulfate salt, phosphate salts and the like. For the purposes of the present description, inorganic salts can be preferred over organic salts. Within the group of inorganic salts, the halides can be preferred over other inorganic salts. Within the halides, the chloride salt can be particularly preferred. Irrespective of which salts are used (organic salts versus inorganic salts, etc), water-soluble salts are preferred as they can be provided in the form of a bee-indigestible composition such as sucrose solutions which can be fed to the bees and thus taken up indirectly by the *Varroa* mites through this route. Whenever reference is made to a specific salt, it always includes the hydrated or anhydrous versions thereof unless otherwise indicated. The group of alkali metals comprises lithium, sodium, potassium, rubidium and caesium. Within the group of alkali metals, lithium is particularly preferred.

Among the alkali metal salts, organic or inorganic salts of lithium which may be hydrated or anhydrous are preferred over the corresponding salts of e.g. potassium. Inorganic lithium salts such as LiCl are advantageous because they cost less as compared to organic lithium salts. Within the group of lithium salts, inorganic lithium salts can thus be preferred over organic lithium salts. Preferred inorganic lithium salts include, but are not limited to, lithium chloride, lithium bromide, lithium nitrate, lithium sulfate, lithium phosphate and the like. However, organic lithium salts can be advantageous because they may complex more than one lithium ion and because they may be taken up by the bees better as compared to inorganic lithium salts, Preferred organic lithium salts include but are not limited to lithium citrate, lithium carbonate, lithium lactate, lithium formate, lithium acetate, lithium trifluoroacetate, lithium maleate, lithium tartrate, lithium orotate and the like. Within the group of inorganic lithium salts, the halides can be preferred over other inorganic salts. Within the group of organic lithium salts, the lactates, citrates, acetates and carbonates can be preferred over other organic salts. One alkali metal salt which is preferred throughout all aspects and embodiments described hereinafter is lithium chloride in hydrated or anhydrous form.

As with other additional agents, alkali metal salts may be administered by a variety of methods, Preferably, the alkali metal salt is topically administered to the ocular surface (conjunctiva and/or cornea) or other anatomical structure of the eye, or to an area adjacent the eye. The alkali metal salt may be included within the spinosyn composition or administered to the subject in a separate composition before, during, or after administration of the spinosyn composition. Preferably; a miticidally effective amount is administered. In some embodiment, the concentration is within the range of about 0.5 mM to about 150 mM alkali metal salt (e.g., LiCl).

Articles of Manufacture

Other aspects of the invention include articles of manufacture useful for carrying out the methods of the invention, such as the spinosyn composition in association with a container; an ocular or facial applicator; and a kit.

One aspect of the invention is an article of manufacture comprising a spinosyn composition disclosed herein; and a container with the topical composition contained therein. Thus, the spinosyn compositions may be contained within a container, which may be accessed for administration to a subject. The container may have a defined interior for containing the composition. Preferably, the composition and container interior are sterile. Examples of containers include a collapsible or non-collapsible tube, bag, packet, blister, strip, ampoule, vial, bottle, can, or jar. The container may be composed of one or more materials appropriate for its use, such as aluminum, polyethylene (e.g., low-density polyethylene (LDPE), high-density polyethylene (HDPE), or polyethylene terephthalate (PET)), polypropylene, or glass.

In some embodiments, the container has a closure such as a cap, which may be actuated to access the composition within the container. Closures used for the purpose of covering the container after the filling process should be as inert as possible, not giving rise to undesired interactions between the contents and the outside environment, and should provide a complete seal. In addition to their protective function, closures should allow the easy and safe administration of the spinosyn composition. In some embodiments, the container has a tamper-evident closure. In some embodiments, the container has no closure and the spinosyn composition is accessed by tearing, separating, or breaking material of the container.

In some embodiments, the container includes a rubber closure (composed of elastomeric material), or a cap and/or overseal which may be composed of aluminum or plastic such as polyethylene, polypropylene.

The container may include a tamper-evident feature, such as a tamper-evident closure. For example, an ophthalmic ointment is typically supplied in small, sterilized, collapsible tubes (containing, e.g., up to about 5 grams of the composition) fitted with a tamper-evident applicator. The tube may include a nozzle shaped so that the ointment can be administered without contaminating what remains in the tube. The container may include a reclosable child-resistant type of closure, such as a "press-turn" or "squeeze-turn" type.

The container may be a single-dose or multi-dose container. In some embodiments, the container is a single-dose container (containing a single dose of the composition for treating an ocular *Demodex* mite infestation of an eye of the human or animal subject, or for treating a condition of the eye or skin associated with ocular *Demodex* mite infestation). In other embodiments, the container is a multi-dose container (containing multiple doses of the composition for treating an ocular *Demodex* mite infestation of an eye of the human or animal subject, or for treating a condition of the eye or skin associated with ocular *Demodex* mite infestation).

Optionally, containers containing a composition described herein are light-proof and have a tight seal. For example, the container(s) can include one of the dermatologically or ophthalmically acceptable spinosyn compositions described herein. In some embodiments, the container protects against certain wavelengths of light and prolonged high temperature, and/or the ingress of air. In some embodiments, the container is a sealed, light-proof container.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Another aspect of the invention is an ocular or facial applicator for treating an ocular *Demodex* mite infestation of an eye of a human or animal subject, or for treating a condition of the eye or skin associated with ocular *Demodex* mite infestation. The applicator is pre-treated with, or contains, a spinosyn composition disclosed herein. The applicator may be used by the subject or by another individual to topically administer a composition comprising one or more spinosyn compounds to the ocular surface (conjunctiva and/or cornea) or other anatomical structure of the eye, or to an area adjacent the eye. In some embodiments, the applicator is a swab, cosmetic pad, wipe, wipe stick, towelette, sponge, gauze, puff, wand, brush, or comb.

Another aspect of the invention is a kit for treating an ocular *Demodex* mite infestation of an eye of a human or animal subject, or for treating a condition of the eye or skin associated with ocular *Demodex* mite infestation. The kit comprises the spinosyn composition and an ocular or facial applicator. The kit may further include a container disclosed herein containing the composition. Examples of applicators include a swab, cosmetic pad, wipe, wipe stick, towelette, sponge, gauze, puff, wand, brush, or comb.

In some embodiments, the applicator is pretreated with, or contains the composition. In this way, when the applicator is pretreated with, or contains the composition, the applicator may function as a container as well.

The kit may include a set of printed or digital instructions for treating an ocular *Demodex* mite infestation of an eye of a human or animal subject, or for treating a condition of the eye or skin associated with ocular *Demodex* mite infestation, by topically administering the composition to the ocular surface (conjunctiva and/or cornea) or other anatomical structure of the eye, or to an area adjacent the eye. For example, the kit may include instructions for use comprising the steps of topically applying the spinosyn composition to an affected area or other target area, and repeating the administration step until sufficient to alleviate or eliminate one or more signs or symptoms associated with *Demodex* infestation, to reduce living *Demodex* count, to eliminate living *Demodex* in a desired area, to reduce *Demodex* re-infestation, or to prevent or delay onset of *Demodex* infestation.

Kits can include packaging material that is compartmentalized to receive one or more containers such as vials, tubes, and the like, each of the container(s) including one of the separate elements to be used in a method described herein. Packaging materials for use in packaging pharmaceutical products include, by way of example only U.S. Pat. Nos. 5,323,907, 5,052,558 and 5,033,252. Examples of pharmaceutical packaging materials include, but are not limited to, blister packs, bottles, tubes, pumps, bags, vials, light-tight sealed containers, syringes, bottles, and any packaging material suitable for a selected formulation and intended mode of administration and treatment.

A kit may include one or more additional containers, each with one or more of various materials desirable from a commercial and user standpoint for use of the compositions for treating *Demodex* described herein. Non-limiting examples of such materials include, but not limited to, buffers, diluents, carrier, package, container, vial and/or tube labels listing contents and/or instructions for use, and package inserts with instructions for use.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In some embodiments of the kit, the spinosyn composition can be presented in a pack or dispenser device which can contain one or more unit dosage forms containing a spinosyn composition disclosed herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a spinosyn composition provided herein formulated in a compatible pharmaceutical carrier can also be prepared, placed in an appropriate container, and labeled for treatment of an indicated condition.

Definitions

As used herein, the term "amplify" refers to increasing the number of copies of a target nucleic acid molecule. The resulting amplification products are called "amplicons." Amplification of a nucleic acid molecule (such as a DNA or RNA molecule) refers to use of a technique that increases the number of copies of a nucleic acid molecule in a sample, for example the number of copies of a *Demodex* (e.g., *D. folliculorum* or *D. brevis*) nucleic acid. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Primer pairs can be used for amplification of a target nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence (e.g., a *Demodex* sequence), for example, by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Methods for preparing and using primers are described in, for example, Sambrook et al. (1989) Molecular Cloning: A Laboratory Manual, Cold Spring Harbor, N.Y.; Ausubel et al. (1987) Current Protocols in Molecular Biology, Greene Publ. Assoc. & Wiley-Intersciences. In one example, a primer includes a label.

Other examples of in vitro amplification techniques include quantitative real-time PCR; reverse transcriptase PCR (RT-PCR); real-time PCR; real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription free amplification (see U.S. Pat. No. 6,025,134), among others.

As used herein, the term "detect" refers to the determination of whether an agent (such as a signal, particular nucleotide, amino acid, nucleic acid molecule, and/or organism) is present or absent, for example, a *Demodex* mite such as *D. folliculorum* and/or *D. brevis*. In some examples, this can further include quantification. For example, use of probes permits detection of a fluorophore, for example, detection of a signal from a fluorophore, which can be used to determine if a nucleic acid corresponding to nucleic acid of *Demodex* (*D. folliculorum* and/or *D. brevis*) is present. The detection of a *D. folliculorum* and/or *D. brevis* nucleic acid molecule indicates the presence of *D. folliculorum* and/or *D. brevis* in the sample, for example a *D. folliculorum* and/or *D. brevis* infestation.

The terms "acaricidal" and "miticidal" are used herein interchangeably to refer to the ability to kill mites of the *Demodex* genus in any life stage, or the ability to interfere with a *Demodex* mite's growth or life cycle in any way that results in an overall reduction in *Demodex* mite population. In some embodiments, the *Demodex* species is *D. folliculorum*, *D. brevis*, or both. For example, the term "miticidal" includes inhibition or elimination of reproductive ability of a pest, as well as inhibition of a pest from progressing from one form to a more mature form, e.g., transition between various larval forms or transition from larvae to proto-nymph or from proto-nymph to nymph, or from nymph to adult. Further, the term miticidal is intended to include all phases of a mite life cycle; thus, for example, the term includes larvicidal, ovicidal, and adulticidal action.

As used herein, the term "miticidally effective" is intended to indicate an amount or concentration of a spinosyn or other miticide that is sufficient to reduce the number of *Demodex* mites in an anatomical locus, as compared to a corresponding anatomical locus in the absence of the amount or concentration of the spinosyn or other miticide.

As used herein, the term "treatment", "treating", and grammatical variations thereof refer to an amelioration, prophylaxis, or reversal of a disease or disorder, or of at least one sign or symptom thereof. In some embodiments, "treatment" or "treating" refers to an amelioration, prophylaxis, or reversal of at least one measurable physical parameter related to the disease or disorder being treated, not necessarily discernible in or by the subject. In yet another embodiment, "treatment" or "treating" refers to inhibiting or slowing the progression of a disease or disorder, either physically, e.g., stabilization of a discernible sign or symptom, physiologically, e.g., stabilization of a physical parameter, or both. In yet another embodiment, "treatment" or "treating" refers to delaying the onset of a disease or disorder.

Exemplified Embodiments

1. A method for treating an ocular *Demodex* mite infestation of an eye of a human or animal subject, or for treating a condition of the eye or skin associated with ocular *Demodex* mite infestation, comprising topically administering a composition comprising one or more spinosyn compounds to the ocular surface (conjunctiva and/or cornea) or other anatomical structure of the eye, or to an area adjacent the eye.

2. The method of embodiment 1, wherein the subject has the condition, and the condition is one or more from among *Demodex*-induced blepharitis (also called *Demodex* blepharitis), *Demodex*-induced ocular rosacea, *Demodex*-induced facial rosacea, dry eye, meibomian gland dysfunction, chalazion, hordeolum, follicular inflammation, non-specific facial dermatitis, infiltrative keratoconjunctivitis, nodular scar deposition, or corneal neovascularization.

3. The method of embodiment 1 or 2, wherein the treatment alleviates one or more signs or symptoms in the subject selected from among: itching, burning, foreign body sensation, crusting and redness of the lid margin, blurry vision, cylindrical dandruff, eyelash misalignment, eyelash trichiasis, eyelash madarosis, lid margin inflammation, meibomian gland dysfunction, blepharoconjunctivitis, and blepharokeratitis.

4. The method of any one of embodiments 1 to 3, wherein the composition is topically administered to an area adjacent to the eye, wherein the area comprises one or more of an eyelid, eyelid margin, eyelashes, eyelash follicles, eyebrow, or eyebrow follicles.

5. The method of any one of embodiments 1 to 3, wherein the composition is topically administered to an area adjacent to the eye, wherein the area comprises a sebaceous gland opening of the eyelid (e.g., one or more of gland of Zeis, gland of Moll, or Meibomian gland).

6. The method of any preceding embodiment, wherein the *Demodex* mite comprises *Demodex folliculorum*, *Demodex brevis*, or both.

7. The method of any preceding embodiment, wherein the subject is symptomatic at the time of said administering.

8. The method of any one of embodiments 1 to 6, wherein the subject is asymptomatic at the time of said administering.

9. The method of any preceding embodiment, further comprising confirming the presence of *Demodex* mites prior to said administering.

10. The method of embodiment 9, wherein the said confirming comprises identifying the *Demodex* mites in vivo or in a biological sample (e.g., hair or skin sample) ex vivo, or detecting a molecule associated with the presence of *Demodex* mites (e.g., chitin, chitin synthase, lipase, *Bacillus* antigen).

11. The method of any preceding embodiment, wherein an effective amount of the composition is topically administered to reduce the number of living *Demodex* mites on the eye and adjacent skin and hair.

12. The method of any preceding embodiment, wherein an effective amount of the composition is topically administered to eliminate the presence of living *Demodex* mites from the eye and adjacent skin and hair.

13. The method of any preceding embodiment, wherein the one or more spinosyn compounds have the chemical structure of formula (I) or a pharmaceutically acceptable salt thereof:

$$\text{(I)}$$

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, can be independently selected from the group consisting of: null; H; F; Cl; Br; I; OH; CN; $(C_{1-4})$ alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid ($-SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone ($=O$); ether ($-OR^{17}$); and ester ($-COOR^{18}$ and $-OC(=O)R^{18}$);

where $R^5$ and $R^7$ can be a double bond within the cyclopentane ring;

where $R^{11}$ and $R^{13}$ can be a double bond within the cyclohexane ring;

where $R^{17}$ can be independently selected from the group consisting of: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl;

where $R^{18}$ can be independently selected from the group consisting of: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl.

14. The method of any preceding embodiment, wherein the one or more spinosyn compounds are selected from among spinosyn A, spinosyn B, spinosyn C, spinosyn D, spinosyn E, spinosyn F, spinosyn G, spinosyn H, spinosyn I, spinosyn J, spinosyn K, spinosyn L, spinosyn M, spinosyn N, spinosyn O, spinosyn P, spinosyn R, spinosyn S, spinosyn T, spinosyn U, spinosyn V, spinosyn W, spinosyn Y, spinosoid N-demethyl D, spinosoid N-demethyl K, spinosoid N,N-didimethyl K, spinosoid N-demethyl P, spinosoid 2'-H A, spinosoid 2'-H D, spinosoid 2'-O-ethyl A, spinosoid 3'-H A, spinosoid 3'-O-ethyl A, spinosoid 3'-O-n-propyl A, spinosoid 3'-O-n-butyl A, spinosoid 3'-O-allyl A, spinosoid $-O-CH_2CF_3$A, spinosoid 4'-H A, spinosoid 4'-O-ethyl A, or spinosoid 2',3',4'-tri-O-ethyl A.

15. The method of any preceding embodiment, wherein the one or more spinosyn compounds comprise a combination of spinosyn A and spinosyn D.

16. The method of embodiment 15, wherein the spinosyn A and spinosyn D are present in the composition in a ratio of about 18:2 to about 16:4 spinosyn A to spinosyn D.

17. The method of embodiment 15, wherein the spinosyn A and spinosyn D are present in the composition in a ratio of about 17:3 spinosyn A to spinosyn D.

18. The method of any preceding embodiment, wherein the composition includes no active agent other than the one or more spinosyn compounds.

19. The method of any one of embodiment 1 to 18, wherein the composition comprises no additional agent that has miticidal activity against the *Demodex* mite.

20. The method of any one of embodiments 1 to 17, wherein the method does not include topical administration of any active agent other than the one or more spinosyn compounds to the ocular surface (conjunctiva and/or cornea) or other anatomical structure of the eye, or to an area adjacent the eye.

21. The method of any one of embodiments 1 to 17, wherein the method does not include topical administration of an agent having miticidal activity against the *Demodex* mite in addition to the one or more spinosyn compounds to the ocular surface (conjunctiva and/or cornea) or other anatomical structure of the eye, or to an area adjacent the eye.

22. The method of any one of embodiments 1 to 17, wherein the composition further comprises an additional agent having miticidal activity against the *Demodex* mite.

23. The method of embodiment 22, wherein the additional agent having miticidal activity against the *Demodex* mite is one or more agents selected from among ivermectin, pyrethrin, pyrethroid (e.g., permethrin, resmethrin, or D-phenothrin), tea tree oil (TTO), TTO component (e.g., terpinen-4-ol (T4O)), metronidazole, hypochlorous acid (HOCl), essential oil (e.g., peppermint oil or *Salvia*), alkali metal salt (e.g., lithium salt), phosphorothioate (e.g., a non-volatile, fat soluble phosphorothioate such as coumaphos), or formamidine (e.g., amitraz).

24. The method of any one of embodiments 1 to 17, further comprising administering an additional agent having miticidal activity against the *Demodex* mite before, during, or after topical administration of the composition with the one or more spinosyn compounds, wherein the additional agent is administered in a separate composition.

25. The method of embodiment 24, wherein the additional agent having miticidal activity against the *Demodex* mite is one or more agents selected from among ivermectin, pyrethrin, pyrethroid (e.g., permethrin, resmethrin, or D-phenothrin), tea tree oil (TTO), TTO component (e.g., terpinen-4-ol (T4O)), metronidazole, hypochlorous acid (HOCl), essential oil (e.g., peppermint oil or *Salvia*), alkali metal salt (e.g., lithium salt), phosphorothioate (e.g., a non-volatile, fat soluble phosphorothioate such as coumaphos), or formamidine (e.g., amitraz).

26. The method of any preceding embodiment, further comprising administering an antibiotic agent to the subject, wherein the antibiotic agent is in the composition with the one or more spinosyn compounds or in a separate composition.

27. The method of embodiment 26, wherein the antibiotic agent has antibacterial activity against one or more of *Streptococci, Staphylococci*, or *Bacillus oleronius*.

28. The method of any preceding embodiment, further comprising administering an anti-inflammatory agent to the subject, wherein the anti-inflammatory agent is in the composition with the one or more spinosyn compounds or in a separate composition.

29. The method of embodiment 28, wherein the anti-inflammatory agent is selected from among a glucocorticoid or other steroid (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drug (e.g., salicylates, arylalkanoic acids, 2-arylpropionic acids, N-arylanthranilic acids, oxicams, coxibs, or sulphonanilides), Cox-2-specific inhibitor (e.g., valdecoxib, celecoxib, or rofecoxib), leflunomide, gold thioglucose, gold thiomalate, aurofin, sulfasalazine, hydroxychloroquinine, minocycline, TNF-alpha binding protein (e.g., infliximab, etanercept, or adalimumab), abatacept, anakinra, interferon-beta, interferon-gamma, interleukin-2, allergy vaccine, antihistamine, antileukotriene, beta-agonists, theophylline, or anticholinergic, antibiotics, tacrolimus, or retinoid.

30. The method of any preceding embodiment, wherein the composition is a solution, suspension, salve, spray, lotion, gel, paste, balm, foam, mousse, scrub or cleanser (e.g., shampoo or soap), cream, or ointment.

31. The method of any preceding embodiment, wherein the composition is topically administered using an applicator (e.g., swab, cosmetic pad, wipe, wipe stick, towelette, sponge, gauze, puff, wand, brush, or comb).

32. The method of any preceding embodiment, wherein the composition is a cosmetic product.

33. The method of embodiment 32, wherein the cosmetic product is a mascara, eye shadow, or eye liner.

34. The method of any preceding embodiment, wherein the composition further comprises one or more excipients selected from among petrolatum, mineral oil, propylparaben, methylparaben, lanolin, chlorobutanol, water, lanolin alcohol, sodium thiosulfate, sodium phosphate monobasic, phenylmercuric acetate, mannitol, zinc chloride, sodium phosphate, potassium acetate, hypromelloses, gentamcicin sulfate, boric acid, sodium hydroxide, lanolin oil, carbomer homopolymer type A or B (allyl pentaerythritol crosslinked), or benzalkonium chloride.

35. The method of any one of embodiments 1 to 34, wherein the composition is an emulsion and further comprises one or more excipients selected from among water, sodium hydroxide, polysorbate 80, glycerine, castor oil, carbomer copolymer type A, sodium acetate, boric acid, sorbic acid, edetate disodium, or silicone oil or silicone polymer gel (e.g., dimethicone or cyclomethicone).

36. The method of any preceding embodiment, wherein the composition further comprises a gelling agent (e.g., gum, agar, carrageenan, petrolatum, or a cellulosic polymer (e.g., hydroxyethyl cellulose or hydroxymethyl cellulose)).

37. The method of any preceding embodiment, further comprising one or more of a solvent, co-solvent, demulcent, emollient, preservative, antioxidant, moisturizer, or solubilizing agent.

38. The method of any preceding embodiment, wherein composition comprises 0.1% to 10% (w/v) of the one or more spinosyn compounds.

39. The method of any preceding embodiment, wherein the composition is accessed and dispensed from a container, with or without a closure (e.g., a cap), prior to administration.

40. The method of embodiment 39, wherein the container is a collapsible or non-collapsible tube, bag, packet, blister, strip, ampoule, viral, bottle, can, or jar.

41. The method of embodiment 39 or 40, wherein the container comprises one or more materials selected from among aluminum, polyethylene (e.g., low-density polyethylene (LDPE), high-density polyethylene (HDPE), or polyethylene terephthalate (PET)), polypropylene, or glass.

42. The method of any one of embodiments 39 to 41, wherein the container is a single-dose container (containing a single dose of the composition for treating an ocular *Demodex* mite infestation of an eye of the human or animal subject, or for treating a condition of the eye or skin caused associated with ocular *Demodex* mite infestation).

43. The method of any one of embodiments 39 to 41, wherein the container is a multi-dose container (containing multiple doses of the composition for treating an ocular *Demodex* mite infestation of an eye of the human or animal subject, or for treating a condition of the eye or skin caused associated with ocular *Demodex* mite infestation).

44. The method of any one of embodiments 39 to 43, wherein the container has an interior containing the composition, and wherein the container interior and the composition are sterile.

45. The method of any preceding embodiment, wherein the composition is a composition of one of Table 1, Table 2, Table 3, Table 4, or Table 5.

46. A topical composition comprising 0.1% to 10% (w/v) of the one or more spinosyn compounds.

47. The topical composition of embodiment 46, wherein the one or more spinosyn compounds have the chemical structure of formula (I) or a pharmaceutically acceptable salt thereof:

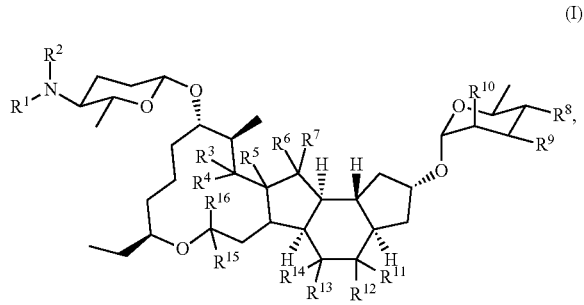

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, can be independently selected from the group consisting of: null; H; F; Cl; Br; I; OH; CN; ($C_{1-4}$) alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxy alkyl; aryloxy; aryl alkoxy; acyloxy; nitro; carbamoyl; trifluoromethyl; phenoxy; benzyloxy; phosphonic acid; phosphate ester; sulfonic acid (—$SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (=O); ether (—$OR^{17}$); and ester (—$COOR^{18}$ and —OC(=O)$R^{18}$);

where $R^5$ and $R^7$ can be a double bond within the cyclopentane ring;

where $R^{11}$ and $R^{13}$ can be a double bond within the cyclohexane ring;

where $R^{17}$ can be independently selected from the group consisting of: a ($C_{1-4}$)alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers; and alkynyl;

where $R^{18}$ can be independently selected from the group consisting of: a ($C_{1-4}$)alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers; and alkynyl.

48. The topical composition of embodiment 46 or 47, wherein the one or more spinosyn compounds comprise a combination of spinosyn A and spinosyn D.

49. The topical composition of embodiment 48, wherein the spinosyn A and spinosyn D are present in the composition in a ratio of about 18:2 to about 16:4 spinosyn A to spinosyn D.

50. The topical composition of embodiment 48, wherein the spinosyn A and spinosyn D are present in the composition in a ratio of about 17:3 spinosyn A to spinosyn D.

51. The topical composition of any one of embodiments 46 to 50, wherein the composition includes no active agent other than the one or more spinosyn compounds.

52. The topical composition of any one of embodiments 46 to 50, wherein the composition comprises no additional agent that has miticidal activity against the *Demodex* mite.

53. The topical composition of any one of embodiments 46 to 50, wherein the composition further comprises an additional agent having miticidal activity against the *Demodex* mite.

54. The topical composition of embodiment 53, wherein the additional agent having miticidal activity against the *Demodex* mite is one or more agents selected from among ivermectin, pyrethrin, pyrethroid (e.g., permethrin, resmethrin, or D-phenothrin), tea tree oil (TTO), TTO component (e.g., terpinen-4-ol (T4O)), metronidazole, hypochlorous acid (HOCl), essential oil (e.g., peppermint oil or *Salvia*), alkali metal salt (e.g., lithium salt), phosphorothioate (e.g., a non-volatile, fat soluble phosphorothioate such as coumaphos), or formamidine (e.g., amitraz).

55. The topical composition of any one of embodiments 46 to 54, further comprising an antibiotic agent.

56. The topical composition of embodiment 55, wherein the antibiotic agent has antibacterial activity against one or more of *Streptococci, Staphylococci*, or *Bacillus oleronius*.

57. The topical composition of any one of embodiments 46 to 56, further comprising an anti-inflammatory agent.

58. The topical composition of embodiment 57, wherein the anti-inflammatory agent is selected from among a glucocorticoid or other steroid (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drug (e.g., salicylates, arylalkanoic acids, 2-arylpropionic acids, N-arylanthranilic acids, oxicams, coxibs, or sulphonanilides), Cox-2-specific inhibitor (e.g., valdecoxib, celecoxib, or rofecoxib), leflunomide, gold thioglucose, gold thiomalate, aurofin, sulfasalazine, hydroxychloroquinine, minocycline, TNF-alpha binding protein (e.g., infliximab, etanercept, or adalimumab), abatacept, anakinra, interferon-beta, interferon-gamma, interleukin-2, allergy vaccine, antihistamine, antileukotriene, beta-agonists, theophylline, or anticholinergic, antibiotics, tacrolimus, or retinoid.

59. The topical composition of any one of embodiments 46 to 58, wherein the composition is a solution, suspension, salve, spray, lotion, gel, paste, balm, foam, mousse, scrub or cleanser (e.g., shampoo or soap), cream, or ointment.

60. The topical composition of any one of embodiments 46 to 59, wherein the composition is a cosmetic product.

61. The topical composition of embodiment 60, wherein the composition is a mascara, eye shadow, or eye liner.

62. The topical composition of any one of embodiments 46 to 61, wherein the composition is an ointment and further comprises one or more excipients selected from among petrolatum, mineral oil, propylparaben, methylparaben, lanolin, chlorobutanol, water, lanolin alcohol, sodium thiosulfate, sodium phosphate monobasic, phenylmercuric acetate, mannitol, zinc chloride, sodium phosphate, potassium acetate, hypromelloses, gentamcicin sulfate, boric acid, sodium hydroxide, lanolin oil, carbomer homopolymer type b (allyl pentaerythritol crosslinked), or benzalkonium chloride.

63. The topical composition of any one of embodiments 46 to 61, wherein the composition is an emulsion and further comprises one or more excipients selected from among water, sodium hydroxide, polysorbate 80, glycerine, castor oil, carbomer copolymer type A, sodium acetate, boric acid, sorbic acid, edetate disodium, carbomer copolymer type a (allyl pentaerythritol crosslinked), or silicone oil or silicone polymer gel (e.g., dimethicone or cyclomethicone).

64. The topical composition of any one of embodiments 46 to 63, wherein the composition further comprises a gelling agent (e.g., gum, agar, carrageenan, petrolatum, or a cellulosic polymer (e.g., hydroxyethyl cellulose or hydroxymethyl cellulose)).

65. The topical composition of any one of embodiments 46 to 64, further comprising one or more of a solvent, co-solvent, demulcent, emollient, preservative, antioxidant, moisturizer, or solubilizing agent.

66. The topical composition of any one of embodiments 46 to 64, wherein the composition is a composition of one of Table 1, Table 2, Table 3, Table 4, or Table 5.

67. An article of manufacture comprising the topical composition of any one of embodiments 46 to 66; and a container with the topical composition contained therein.

68. The article of embodiment 67, wherein the container has a closure (e.g., a cap), which may be actuated to access the composition within the container. 69. The article of embodiment 67 or 68, wherein the container is a collapsible or non-collapsible tube, bag, packet, blister, strip, ampoule, vial, bottle, can, or jar.

70. The article of any one of embodiments 67 to 69, wherein the container comprises one or more materials selected from among aluminum, polyethylene (e.g., low-density polyethylene (LDPE), high-density polyethylene (HDPE), or polyethylene terephthalate (PET)), polypropylene, or glass.

71. The article of any one of embodiments 67 to 70, wherein the container is a single-dose container (containing a single dose of the composition for treating an ocular *Demodex* mite infestation of an eye of the human or animal subject, or for treating a condition of the eye or skin associated with ocular *Demodex* mite infestation).

72. The article of any one of embodiments 67 to 70, wherein the container is a multi-dose container (containing multiple doses of the composition for treating an ocular *Demodex* mite infestation of an eye of the human or animal subject, or for treating a condition of the eye or skin associated with ocular *Demodex* mite infestation).

73. The article of any one of embodiments 67 to 72, wherein the container has an interior containing the composition, and wherein the container interior and the composition are sterile.

74. An ocular or facial applicator pre-treated with, or containing, the topical composition of any one of embodiments 46 to 66.

75. The ocular or facial applicator of embodiment 74, wherein the applicator is a swab, cosmetic pad, wipe, wipe stick, towelette, sponge, gauze, puff, wand, brush, or comb.

76. A kit comprising the topical composition of any one of embodiments 46 to 66; and an ocular or facial applicator.

77. The kit of embodiment 76, wherein the kit further comprises a container containing the composition.

78. The kit of embodiment 76, wherein the applicator is pretreated with, or containing the composition.

79. The kit of any one of embodiments 76 to 78, wherein the applicator is a swab, cosmetic pad, wipe, wipe stick, towelette, sponge, gauze, puff, wand, brush, or comb.

80. The kit of any one of embodiments 76 to 79, further comprising instructions for treating an ocular *Demodex* mite infestation of an eye of a human or animal subject, or for treating a condition of the eye or skin associated with ocular *Demodex* mite infestation, by topically administering the composition to the ocular surface (conjunctiva and/or cornea) or other anatomical structure of the eye, or to an area adjacent the eye.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A method for treating an ocular *Demodex* mite infestation of an eye of a human or animal subject, comprising topically administering a miticidally effective amount of a composition comprising one or more spinosyn compounds to one or more anatomical sites of the eye selected from among an eyelid, eyelid margin, eyelash, eyelash follicles, eyebrow, eyebrow follicles, or corner of the eye, wherein the ocular *Demodex* mite infestation is present at the time the composition is topically administered.

2. The method of claim 1, wherein the composition comprises 0.1% to 10% (w/v) of the one or more spinosyn compounds.

3. The method of claim 1, wherein the subject has a condition of the eye or skin associated with ocular *Demodex* mite infestation at the time the composition is topically administered, and the condition is one or more from among *Demodex*-induced blepharitis (also called *Demodex* blepharitis), *Demodex*-induced ocular rosacea, *Demodex*-induced facial rosacea, dry eye, meibomian gland dysfunction, chalazion, hordeolum, follicular inflammation, non-specific facial dermatitis, infiltrative keratoconjunctivitis, nodular scar deposition, or corneal neovascularization.

4. The method of claim 1, wherein the treatment alleviates one or more signs or symptoms in the subject selected from among: itching, burning, foreign body sensation, crusting and redness of the lid margin, blurry vision, cylindrical dandruff, eyelash misalignment, eyelash trichiasis, eyelash madarosis, lid margin inflammation, meibomian gland dysfunction, blepharoconjunctivitis, and blepharokeratitis.

5. The method of claim 1, further comprising confirming the presence of *Demodex* mites prior to said administering, wherein said confirming comprises identifying the *Demodex* mites in vivo or in a biological sample ex vivo, or detecting a molecule associated with the presence of *Demodex* mites.

6. The method of claim 1, wherein the *Demodex* mite comprises *Demodex folliculorum* mites, *Demodex brevis* mites, or both *Demodex folliculorum* mites and *Demodex brevis* mites.

7. The method of claim 1, wherein the one or more spinosyn compounds have the chemical structure of formula (I) or a pharmaceutically acceptable salt thereof:

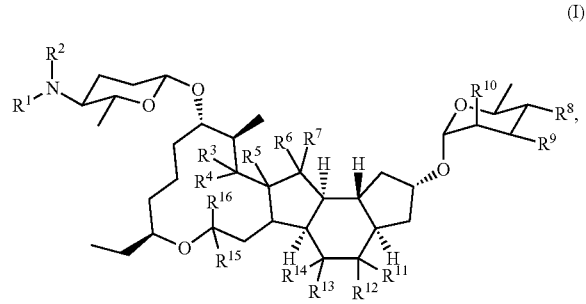

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, can be independently selected from the group consisting of: null; H; F; Cl; Br; I; OH; CN; $(C_{1-4})$alkyl, such as methyl, ethyl, n-propyl, isopropyl, n-butyl, sec-butyl, isobutyl, tert-butyl; $(C_{2-4})$ alkenyl, such as ethenyl, propenyl, butenyl, where the double bond can be located at any position in the alkenyl carbon chain, and including any alkenyl conformational isomers; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid (—$SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (=O); ether (—$OR^{17}$); and ester (—$COOR^{18}$ and —OC(=O)$R^{18}$);

where $R^5$ and $R^7$ can be a double bond within the cyclopentane ring;

where $R^{11}$ and $R^{13}$ can be a double bond within the cyclohexane ring;

where $R^{17}$ can be independently selected from the group consisting of: a ($C_{1-4}$)alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers; and alkynyl;

where $R^{18}$ can be independently selected from the group consisting of: a ($C_{1-4}$)alkyl, such as methyl, ethyl, n-propyl, isopropyl, n-butyl, sec-butyl, isobutyl, tert-butyl; ($C_{2-4}$)alkenyl, such as ethenyl, propenyl, butenyl, where the double bond can be located at any position in the alkenyl carbon chain, and including any alkenyl conformational isomers; and alkynyl.

8. The method of claim 1, wherein the one or more spinosyn compounds comprise a combination of spinosyn A and spinosyn D.

9. The method of claim 1, wherein the one or more spinosyn compounds is spinosad.

10. The method of claim 1, wherein the composition includes no active agent other than the one or more spinosyn compounds.

11. The method of claim 1, wherein the composition comprises no additional agent that has miticidal activity against the Demodex mite.

12. The method of claim 1, wherein the composition further comprises an additional agent having miticidal activity against the Demodex mite.

13. The method of claim 12, wherein the additional agent having miticidal activity against the Demodex mite is one or more agents selected from among ivermectin, pyrethrin, pyrethroid, tea tree oil (TTO), TTO component, metronidazole, hypochlorous acid (HOCl), essential oil, alkali metal salt, phosphorothioate, or formamidine.

14. The method of claim 1, wherein the composition further comprises an antibiotic agent.

15. The method of claim 14, wherein the antibiotic agent has antibacterial activity against one or more of Streptococci, Staphylococci, or Bacillus oleronius.

16. The method of claim 1, wherein the composition is a suspension or emulsion.

17. The method of claim 1, wherein the composition is an ointment and further comprises one or more excipients selected from among petrolatum, mineral oil, propylparaben, methylparaben, lanolin, chlorobutanol, water, lanolin alcohol, sodium thiosulfate, sodium phosphate monobasic, phenylmercuric acetate, mannitol, zinc chloride, sodium phosphate, potassium acetate, hypromelloses, gentamcicin sulfate, boric acid, sodium hydroxide, lanolin oil, carbomer homopolymer tybe b (allyl pentaerythritol crosslinked), or benzalkonium chloride, or wherein the composition is an emulsion and further comprises one or more excipients selected from among water, sodium hydroxide, polysorbate 80, glycerine, castor oil, carbomer copolymer type A, sodium acetate, boric acid, sorbic acid, edetate disodium, carbomer copolymer type a (allyl pentaerythritol crosslinked), or silicone oil or silicone polymer gel.

18. The method of claim 1, wherein the subject is human.

19. The method of claim 1, wherein the ocular Demodex mite infestation is thereby treated.

20. A method for treating an ocular Demodex mite infestation of an eye of a human or animal subject, or for treating a condition of the eye or skin associated with ocular Demodex mite infestation, comprising topically administering a miticidally effective amount of a composition comprising one or more spinosyn compounds to one or more anatomical sites of the eye selected from among an eyelid, eyelid margin, eyelash, eyelash follicle, eyebrow, eyebrow follicles, or corner of the eye, further comprising confirming the presence of Demodex mites prior to said administering, wherein said confirming comprises identifying the Demodex mites in vivo or in a biological sample ex vivo, or detecting a molecule associated with the presence of Demodex mites.

* * * * *

UNITED STATES PATENT AND TRADEMARK OFFICE
CERTIFICATE OF CORRECTION

PATENT NO. : 10,730,901 B2  
APPLICATION NO. : 16/523984  
DATED : August 4, 2020  
INVENTOR(S) : Carlos Santos, Iuan-bor Chen and Josue Moran Page 1 of 1

It is certified that error appears in the above-identified patent and that said Letters Patent is hereby corrected as shown below:

In the Specification

Column 5,
Line 18, "$R^{10}$=—$OR^{17}$," should read --$R^{10}$= -$OR^{17}$,--.
Line 24, "$R^{10}$=—$OR^{17}$," should read --$R^{10}$= -$OR^{17}$,--.

Column 23,
Line 61, "salts, Preferred" should read --salts. Preferred--.

Column 27,
Line 37, "transcription free" should read --transcription-free--.

Signed and Sealed this
Twenty-fourth Day of November, 2020

Andrei Iancu
*Director of the United States Patent and Trademark Office*